(12) United States Patent
Ashe et al.

(10) Patent No.: US 9,200,068 B2
(45) Date of Patent: Dec. 1, 2015

(54) COMPOSITIONS AND METHODS RELATED TO TAUOPATHY

(71) Applicant: Regents of the University of Minnesota, Minneapolis, MN (US)

(72) Inventors: Karen Hsiao Ashe, North Oaks, MN (US); Xiaohui Zhao, Woodbury, MN (US); Michael Anthony Walters, Minneapolis, MN (US); Derek John Hook, San Diego, CA (US); Morgan Clotaire Paul Le Naour, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 14/133,061

(22) Filed: Dec. 18, 2013

(65) Prior Publication Data
US 2014/0171373 A1 Jun. 19, 2014

Related U.S. Application Data

(60) Provisional application No. 61/738,510, filed on Dec. 18, 2012.

(51) Int. Cl.
| C07K 16/18 | (2006.01) |
| C12Q 1/37 | (2006.01) |
| A61K 38/00 | (2006.01) |
| C07K 14/47 | (2006.01) |

(52) U.S. Cl.
CPC .............. *C07K 16/18* (2013.01); *C07K 14/4711* (2013.01); *C12Q 1/37* (2013.01); *A61K 38/00* (2013.01); *C07K 2317/34* (2013.01); *G01N 2500/04* (2013.01); *G01N 2800/2821* (2013.01)

(58) Field of Classification Search
CPC ........... A61K 39/395; A61K 39/39533; C07K 16/18; C07K 2317/34
See application file for complete search history.

(56) References Cited

U.S. PATENT DOCUMENTS

| 5,843,779 | A | 12/1998 | Vandermeeren et al. |
| 5,861,257 | A | 1/1999 | Vandermeeren et al. |
| 6,008,024 | A | 12/1999 | Vandermeeren et al. |
| 6,010,913 | A | 1/2000 | Vandermeeren et al. |
| 6,121,003 | A | 9/2000 | VanMechelen et al. |
| 6,232,437 | B1 | 5/2001 | Vandermeeren et al. |
| 6,238,892 | B1 | 5/2001 | Mercken et al. |
| 6,500,674 | B1 | 12/2002 | Vandermeeren et al. |
| 6,797,478 | B1 | 9/2004 | Zemlan et al. |
| 6,803,233 | B2 | 10/2004 | Lynch et al. |
| 6,875,578 | B2 | 4/2005 | Giuliano et al. |
| 6,900,293 | B2 | 5/2005 | Mercken et al. |
| 7,273,964 | B1 | 9/2007 | Cattaneo et al. |
| 7,442,516 | B2 | 10/2008 | Ohno et al. |
| 7,888,050 | B2 | 2/2011 | Reagan et al. |
| 8,017,385 | B2 | 9/2011 | Kaplitt et al. |
| 8,114,617 | B2 | 2/2012 | Reagan et al. |
| 8,163,873 | B2 | 4/2012 | Mercken et al. |
| 2008/0050383 | A1* | 2/2008 | Sigurdsson et al. ....... 424/141.1 |
| 2008/0107601 | A1 | 5/2008 | Lauwereys et al. |
| 2008/0311051 | A1 | 12/2008 | Chauvier et al. |
| 2009/0042805 | A1 | 2/2009 | Chauvier et al. |
| 2009/0123936 | A1* | 5/2009 | Novak .......................... 435/7.1 |
| 2010/0184703 | A1 | 7/2010 | Casimir et al. |
| 2011/0312059 | A1 | 12/2011 | Moe et al. |
| 2012/0196892 | A1 | 8/2012 | Chauvier |

FOREIGN PATENT DOCUMENTS

| EP | 1 995 255 A1 | 11/2008 |
| WO | 2006/056487 A2 | 6/2006 |
| WO | 2010/021755 A2 | 2/2010 |
| WO | 2013/036840 A2 | 3/2013 |
| WO | 2013/123266 A1 | 8/2013 |

OTHER PUBLICATIONS

Schweizer et al. 2007 "Inhibition of Caspase-2 by a designed ankyrin repeat protein: specificity, structure, and inhibition mechanism" Structure 15:625-636.*
Abraha et al. 2000 "C-terminal inhibition of tau assembly in vitro and in Alzheimer's disease" J cell Sci 113:3737-3745.*
Ghoshal et al. 2001 "Tau-66: evidence for a novel tau conformation in alzheimer's disease" J Neurochem 77:1372-1385.*
Arai et al., "Heteroduplex Joint Formation by a Stoichiometric Complex of Rad51 and Rad52 of *Saccharomyces cerevisiae*," *J. Biol. Chem.*, Sep. 16, 2005; 280(37):32218-32229. Available online Jul. 19, 2005.
Ashe et al., "A Tale about Tau," *NEJM*, 2007; 357:933-935.
Ashe et al., "Probing the Biology of Alzheimer's Disease in Mice," *Neuron*, Jun. 10, 2010; 66(5):631-645.

(Continued)

*Primary Examiner* — Gregory S Emch
*Assistant Examiner* — Adam M Weidner
(74) *Attorney, Agent, or Firm* — Mueting, Raasch & Gebhardt, P.A.

(57) ABSTRACT

Disclosed herein are isolated polypeptides, antibody preparations, treatment methods, diagnostic methods, and screening methods related to tauopathy. Generally, the isolated polypeptide includes a core pentapeptide, with the proviso that the isolated polypeptide is not a native full-length tau protein. Generally, the antibody preparations include antibody that specifically binds to SEQ ID NO:12. Generally, the treatment methods include administering to a subject a composition that includes the isolated polypeptide. Generally, the diagnostic methods includes contacting a sample from a subject with an antibody preparation that includes antibody that specifically binds to SEQ ID NO:12, and then detecting a ligand in the sample that specifically binds the antibody preparation. Generally, the screening method includes incubating a mixture of caspase-2, a labeled caspase-2 cleavage substrate, and a test compound under conditions effective to permit the caspase-2 to cleave the caspase-2 cleavage substrate, then determining whether the test compound inhibits cleavage of the substrate by caspase-2.

6 Claims, 19 Drawing Sheets

(56) References Cited

OTHER PUBLICATIONS

Bennett et al., "The Rush Memory and Aging Project: Study Design and Baseline Characteristics of the Study Cohort," *Neuroepidemiology*, 2005; 25:163-175. Available online Aug. 15, 2005.

Berger et al., "Accumulation of Pathological Tau Species and Memory Loss in a Conditional Model of Tauopathy," *The Journal of Neuroscience*, Apr. 4, 2007; 27(14):3650-3662.

Bergeron et al., "Defects in regulation of apoptosis in caspase-2-deficient mice," *Genes & Development*, May 1, 1998: 12:1304-1314.

Bi et al., "Novel Cathepsin D Inhibitors Block the Formation of Hyperphosphorylated Tau Fragments in Hippocampus," *Journal of Neurochemistry*, Apr. 2000; 74(4):1469-1477.

Celtek Peptides, Celtek Bioscience, LLC, Custom Peptide Quotation No. 62758-13; Jun. 3, 2011; 1 page.

Celtek Peptides, Celtek Bioscience, LLC, Custom Peptide Quotation No. 62758-14; Jul. 19, 2011; 1 page.

Chauvier et al., "Targeting neonatal ischemic brain injury with a pentapeptide-based irreversible caspase inhibitor," *Cell Death and Disease*, 2011; 2:e203.

Cleary et al., "Natural oligomers of the amyloid-β protein specifically disrupt cognitive function," *Nature Neuroscience*, 2005; 8:79-84.

Cotman et al., "The Role of Caspase Cleavage of Tau in Alzheimer Disease Neuropathology," *J. Neuropathol Exp Neurol*, Feb. 2005; 64(2):104-112.

de Calignon et al., "Caspase activation precedes and leads to tangles," *Nature*, Apr. 22, 2010; 464(7292):1201-1204.

Ferreira et al., "Calpain-Mediated Tau Cleavage: A Mechanism Leading to Neurodegeneration Shared by Multiple Tauopathies," *Molecular Medicine*, Jul.-Aug. 2011, 17(7-8):676-685.

Gamblin et al., "Caspase cleavage of tau: Linking amyloid and neurofibrillary tangles in Alzheimer's disease," *PNAS USA*, Aug. 19, 2003; 100(17):10032-10037. Available online Jul. 29, 2003.

Garg et al., "Cleavage of Tau by calpain in Alzheimer's disease: the quest for the toxic 17 kD fragment," *Neurobiology of Aging*, Jan. 2011; 32(1):1-14. Available online Oct. 21, 2010.

Goedert et al., "Cloning and sequencing of the cDNA encoding an isoform of microtubule-associated protein tau containing four tandem repeats: differential expression of tau protein mRNAs in human brain," *The EMBO Journal*, 1989; 8(2):393-399.

Graham et al., "Cleavage at the caspase-6 site is required for neuronal dysfunction and degeneration due to mutant huntingtin," *Cell*, Jun. 16, 2006; 125(6):1179-1191.

Gravitz, "Drugs: A tangled web of targets," *Nature*, Jul. 14, 2011; 475:S9-S11.

Guo et al., "Active Caspase-6 and Caspase-6-Cleaved Tau in Neuropil Threads, Neuritic Plaques, and Neurofibrillary Tangles of Alzheimer's Disease," *Am. J. Path.*, Aug. 2004; 165(2):523-531.

Herrup et al., "Cell cycle regulation in the postmitotic neuron: oxymoron or new biology?" *Nature Reviews Neuroscience*, May 2007; 8:368-378.

Hoover et al., "Tau Mislocalization to Dendritic Spines Mediates Synaptic Dysfunction Independently of Neurodegeneration," *Neuron*, Dec. 22, 2010; 68(6):1067-1081.

Ittner et al., "Dendritic Function of Tau Mediates Amyloid-β Toxicity in Alzheimer's Disease Mouse Models," *Cell*, Aug. 6, 2010; 142(3):387-397.

Jack et al., "Hypothetical model of dynamic biomarkers of the Alzheimer's pathological cascade," *The Lancet Neurology*, Jan. 2010; 9(1):119-128.

Kitevska et al., "Caspase-2: controversial killer or checkpoint controller?" *Apoptosis*, Jul. 2009; 14(7):829-848.

Lane, "Beyond amyloid: a diverse portfolio of novel drug discovery programs for Alzheimer's disease and related dementias," *Alz. Res. Ther.*, Dec. 20, 2011; 3:36.

Lesne et al., "A specific amyloid-β protein assembly in the brain impairs memory," *Nature*, Mar. 16, 2006; 440:352-357.

Lin et al., "Modulation of calcium/calmodulin kinase-II provides partial neuroprotection against beta-amyloid peptide toxicity," *Eur. J. Neuroscience*, Apr. 16, 2004; 19(8):2047-2055.

Lin et al., "Immunoelectron Microscopic and Biochemical Studies of Caspase-Cleaved Tau in a Mouse Model of Tauopathy," *J. Neuropath. & Exp Neuro.*, Sep. 2011; 70(9):779-787.

Liu et al., "Dual vulnerability of tau to calpains and caspase-3 proteolysis under neurotoxic and neurodegenerative conditions," *ASN Neuro*, Jan./Feb. 2011; 3(1):e00051.

Maillard et al., "Exploiting differences in caspase-2 and -3 $S_2$ subsites for selectivity: structure-based design, solid-phase synthesis and in vitro activity of novel substrate-based caspase-2 inhibitors," *Bioorg Med Chem*, Oct. 1, 2011; 19(19):5833-5851.

Mayford et al., "Control of Memory Formation Through Regulated Expression of a CaMKII Transgene," *Science*, Dec. 6, 1996; 274(5293):1678-1683.

Newman et al., "Caspase-cleaved tau accumulation in neurodegenerative diseases associated with tau and α-synuclein pathology," *Acta Neuropathologica*, Aug. 2005; 110(2):135-144.

Park et al., "The Generation of a 17 kDa Neurotoxic Fragment: An Alternative Mechanism by which Tau Mediates β-Amyloid-Induced Neurodegeneration," *J. Neurosci.*, Jun. 1, 2005; 25(22):5365-5375.

Pozueta et al., "Caspase-2 is required for dendritic spine and behavioural alterations in J20 APP transgenic mice," *Nat. Commun.*, Jun. 10, 2013; 4(1939).

Ramsden et al., "Age-Dependent Neurofibrillary Tangle Formation, Neuron Loss, and Memory Impairment in a Mouse Model of Human Tauopathy (P301L)," *J. Neurosci.*, Nov. 16, 2005; 25:10637-10647.

Roberson et al., "Reducing Endogenous Tau Ameliorates Amyloidβ-Induced Deficits in an Alzheimer's Disease Mouse Model," *Science*, May 4, 2007; 316(5825):750-754.

Ryan et al., "Amyloid-_42 signals tau hyperphosphorylation and compromises neuronal viability by disrupting alkylacylglycerophosphocholine metabolism," *PNAS*, Dec. 8, 2009; 106(49):20936-20941.

SantaCruz et al., "Tau Suppression in a Neurodegenerative Mouse Model Improves Memory Function," *Science*, Jul. 15, 2005; 309(5733):476-481.

Takemura et al., "DNA Aptamers That Bind to $PrP^C$ and Not $PrP^{Sc}$ Show Sequence and Structure Specificity," *Exp. Biol., Med.*, Feb. 2006; 231:204-214.

Tang et al., "Structural and Enzymatic Insights into Caspase-2 Protein Substrate Recognition and Catalysis," *The Journal of Biological Chemistry*, Sep. 30, 2011; 286(39):34147-34154.

Troy et al., "Caspase-2 Mediates Neuronal Cell Death Induced by b-Amyloid," *Journal of Neuroscience*, Feb. 15, 2000; 20(4):1366-1392.

Vakifahmetoglu-Norberg et al., "The unpredictable caspase-2: what can it do?" *Trends in Cell Biology*, Mar. 2010; 20(3):150-159. Available online Jan. 12, 2010.

Westerman et al., "The Relationship between Aβ and Memory in the Tg2576 Mouse Model of Alzheimer's Disease," *J. Neurosci.*, Mar. 1, 2002; 22(5):1858-1867.

Wolfer et al., "Extended analysis of path data from mutant mice using the public domain software Wintrack," *Physiol Behav.*, Aug. 2001; 73(5):745-753.

Wongphatcharachai et al., "Neutralizing DNA Aptamers against Swine Influenza H3N2 Viruses," *J. Clin. Microbiol.*, 2013; 51:46-54.

Wu et al., "Specific Cleavage of Recombinant Protein t3 between Valine-220 and Tyrosine-221 (val-309 and tyr-310 of t4) by a Double-Stranded DNA-Stimulated Protease," *Biochemical and Biophysical Research Communications*, 1996; 221:248-253.

Yue et al., "Sex difference in pathology and memory decline in rTg4510 mouse model of tauopathy," *Neurobiology of Aging*, 2009; 32(2011):590-603. Available on line May 7, 2009.

Zemlan et al., "Quantification of Axonal Damage in Traumatic Brain Injury: Affinity Purification and Characterization of Cerebrospinal Fluid Tau Proteins," *Journal of Neurochemistry*, 1999; 72(2):741-750.

\* cited by examiner

Fig. 2
A
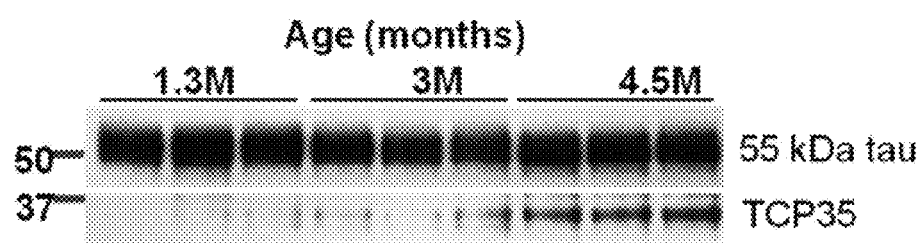
B
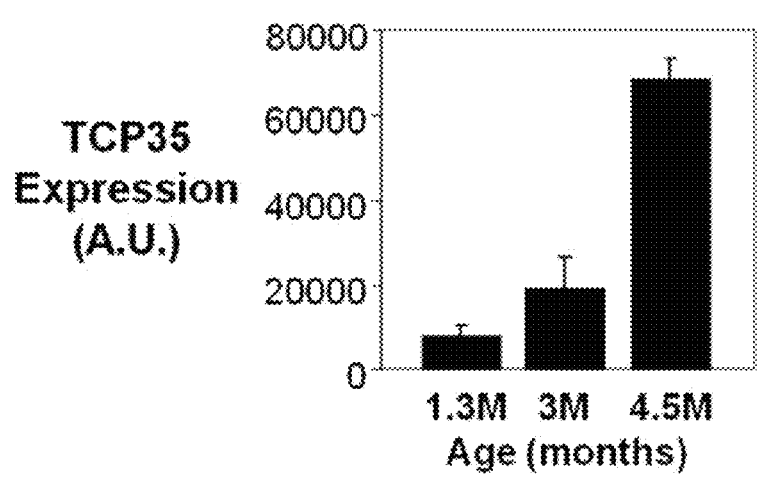
C
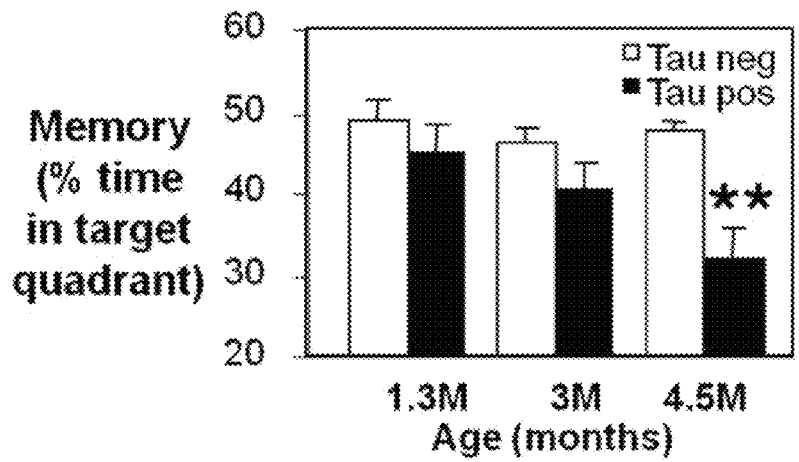

Fig. 18
A
| | $P_6$ | $P_5$ | $P_4$ | $P_3$ | $P_2$ | $P_1$ (D314) | $P_1'$ | |
|---|---|---|---|---|---|---|---|---|
| | | Y | K | P | V | D | | (→ cleavage sequence) |
| | | V | D | V | A | D | | (→ canonical sequence) |
B
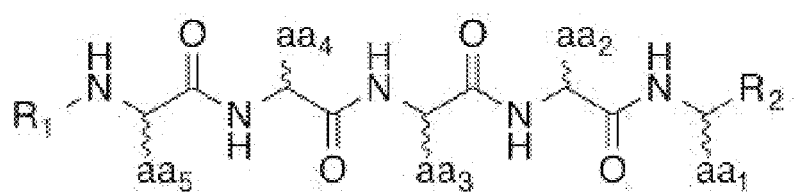
C
$R_2 =$
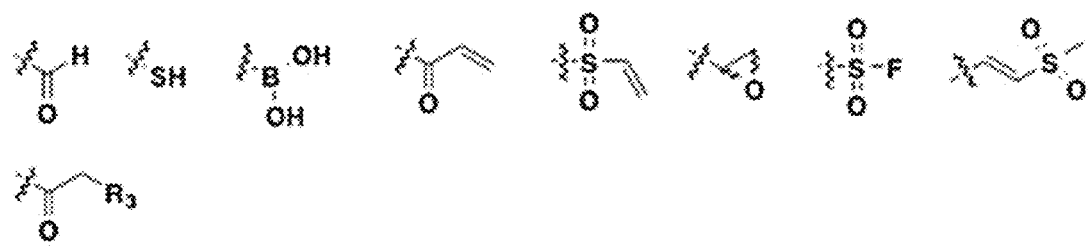
$R_3 =$
F, Cl, Br
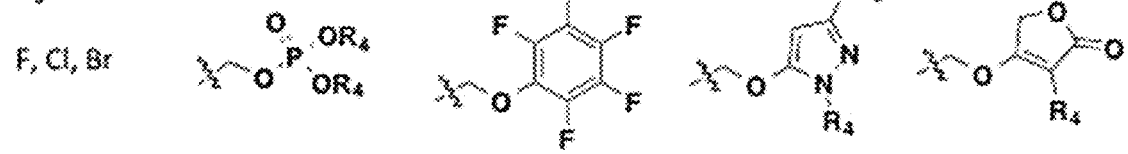

Fig. 19
A 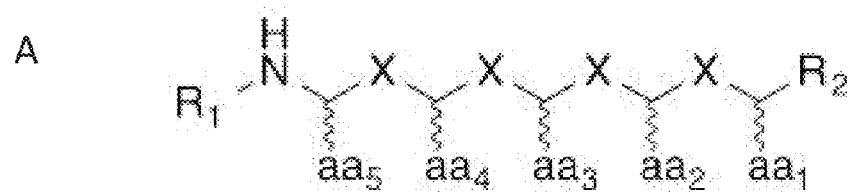
B 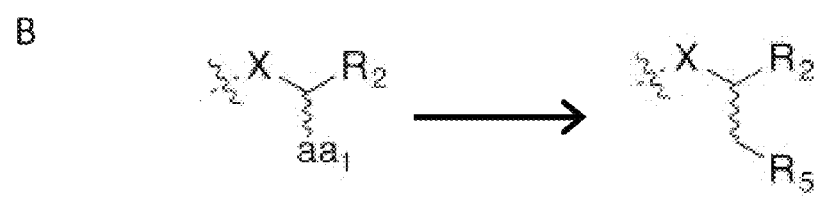
C
R₂=
R₃=
F, Cl, Br 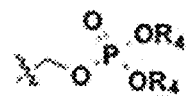 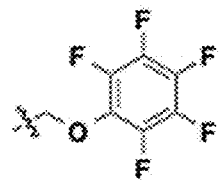 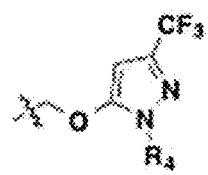 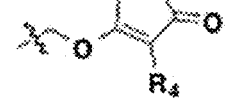

SEQUENCE LISTING

```
<160> NUMBER OF SEQ ID NOS: 38

<210> SEQ ID NO 1
<211> LENGTH: 5
<212> TYPE: PRT
<213> ORGANISM: artificial
<220> FEATURE:
<223> OTHER INFORMATION: caspase-2 inhibitor peptide
<220> FEATURE:
<221> NAME/KEY: MOD_RES
<222> LOCATION: (1)..(1)
<223> OTHER INFORMATION: METHYLATION
<220> FEATURE:
```

-continued

```
<221> NAME/KEY: MOD_RES
<222> LOCATION: (5)..(5)
<223> OTHER INFORMATION: ALDEHYDE GROUP

<400> SEQUENCE: 1

Tyr Lys Pro Val Asp
1               5

<210> SEQ ID NO 2
<211> LENGTH: 16
<212> TYPE: PRT
<213> ORGANISM: artificial
<220> FEATURE:
<223> OTHER INFORMATION: synthetic caspase-2 substrate sequence
<220> FEATURE:
<221> NAME/KEY: MISC_FEATURE
<222> LOCATION: (1)..(1)
<223> OTHER INFORMATION: Fluorescein isothiocyanate (FITC)
<220> FEATURE:
<221> NAME/KEY: MISC_FEATURE
<222> LOCATION: (1)..(1)
<223> OTHER INFORMATION: Aminocaproic acid (AHX) lysine
      derivative/analogue
<220> FEATURE:
<221> NAME/KEY: MISC_FEATURE
<222> LOCATION: (16)..(16)
<223> OTHER INFORMATION: CARBOXYLIC ACID GROUP

<400> SEQUENCE: 2

Gly Ser Val Gln Ile Val Tyr Lys Pro Asp Leu Ser Lys Val Thr Ser
1               5                   10                  15

<210> SEQ ID NO 3
<211> LENGTH: 11
<212> TYPE: PRT
<213> ORGANISM: artificial
<220> FEATURE:
<223> OTHER INFORMATION: caspase-2 cleavage product
<220> FEATURE:
<221> NAME/KEY: MISC_FEATURE
<222> LOCATION: (1)..(1)
<223> OTHER INFORMATION: Fluorescein isothiocyanate (FITC)
<220> FEATURE:
<221> NAME/KEY: MISC_FEATURE
<222> LOCATION: (1)..(1)
<223> OTHER INFORMATION: Aminocaproic acid (AHX) lysine
      derivative/analogue
<220> FEATURE:
<221> NAME/KEY: MISC_FEATURE
<222> LOCATION: (1)..(1)
<223> OTHER INFORMATION: Aminocaproic acid (AHX) lysine
      derivative/analogue

<400> SEQUENCE: 3

Gly Ser Val Gln Ile Val Tyr Lys Pro Val Asp
1               5                   10

<210> SEQ ID NO 4
<211> LENGTH: 17
<212> TYPE: PRT
<213> ORGANISM: artificial
<220> FEATURE:
<223> OTHER INFORMATION: synthetic caspase-2 substrate sequence
<220> FEATURE:
<221> NAME/KEY: MISC_FEATURE
<222> LOCATION: (1)..(1)
<223> OTHER INFORMATION: Fluorescein isothiocyanate (FITC)
<220> FEATURE:
<221> NAME/KEY: MISC_FEATURE
<222> LOCATION: (1)..(1)
<223> OTHER INFORMATION: Aminocaproic acid (AHX) lysine
      derivative/analogue
<220> FEATURE:
```

```
<221> NAME/KEY: MOD_RES
<222> LOCATION: (8)..(8)
<223> OTHER INFORMATION: ACETYLATION
<220> FEATURE:
<221> NAME/KEY: MISC_FEATURE
<222> LOCATION: (17)..(17)
<223> OTHER INFORMATION: CARBOXYLIC ACID GROUP

<400> SEQUENCE: 4

Gly Ser Val Gln Ile Val Tyr Lys Pro Val Asp Leu Ser Lys Val Thr
1               5                   10                  15

Ser

<210> SEQ ID NO 5
<211> LENGTH: 11
<212> TYPE: PRT
<213> ORGANISM: artificial
<220> FEATURE:
<223> OTHER INFORMATION: caspase-2 cleavage product
<220> FEATURE:
<221> NAME/KEY: MISC_FEATURE
<222> LOCATION: (1)..(1)
<223> OTHER INFORMATION: Fluorescein isothiocyanate (FITC)
<220> FEATURE:
<221> NAME/KEY: MISC_FEATURE
<222> LOCATION: (1)..(1)
<223> OTHER INFORMATION: Aminocaproic acid (AHX) lysine
      derivative/analogue
<220> FEATURE:
<221> NAME/KEY: MOD_RES
<222> LOCATION: (8)..(8)
<223> OTHER INFORMATION: ACETYLATION
<220> FEATURE:
<221> NAME/KEY: MISC_FEATURE
<222> LOCATION: (11)..(11)
<223> OTHER INFORMATION: CARBOXYLIC ACID GROUP

<400> SEQUENCE: 5

Gly Ser Val Gln Ile Val Tyr Lys Pro Val Asp
1               5                   10

<210> SEQ ID NO 6
<211> LENGTH: 22
<212> TYPE: DNA
<213> ORGANISM: artificial
<220> FEATURE:
<223> OTHER INFORMATION: synthetic oligonucleotide primer

<400> SEQUENCE: 6
gattaacagc gcattagagc tg                                          22

<210> SEQ ID NO 7
<211> LENGTH: 27
<212> TYPE: DNA
<213> ORGANISM: artificial
<220> FEATURE:
<223> OTHER INFORMATION: synthetic oligonucleotide primer

<400> SEQUENCE: 7
gcatatgatc aattcaaggc cgataag                                     27

<210> SEQ ID NO 8
<211> LENGTH: 20
<212> TYPE: DNA
<213> ORGANISM: artificial
<220> FEATURE:
<223> OTHER INFORMATION: synthetic oligonucleotide primer

<400> SEQUENCE: 8
```

```
tgaaccagga tggctgagcc                                                    20
```

<210> SEQ ID NO 9
<211> LENGTH: 22
<212> TYPE: DNA
<213> ORGANISM: artificial
<220> FEATURE:
<223> OTHER INFORMATION: synthetic oligonucleotide primer

<400> SEQUENCE: 9

```
ttgtcatcgc ttccagtccc cg                                                 22
```

<210> SEQ ID NO 10
<211> LENGTH: 8
<212> TYPE: PRT
<213> ORGANISM: artificial
<220> FEATURE:
<223> OTHER INFORMATION: antibody binding sequence
<220> FEATURE:
<221> NAME/KEY: MOD_RES
<222> LOCATION: (1)..(1)
<223> OTHER INFORMATION: ACETYLATION

<400> SEQUENCE: 10

```
Cys Ile Val Tyr Lys Pro Val Asp
1               5
```

<210> SEQ ID NO 11
<211> LENGTH: 13
<212> TYPE: PRT
<213> ORGANISM: artificial
<220> FEATURE:
<223> OTHER INFORMATION: antigen peptide sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (13)..(13)
<223> OTHER INFORMATION: AMIDATION

<400> SEQUENCE: 11

```
Cys Ile Val Tyr Lys Pro Val Asp Leu Ser Lys Val Thr
1               5                   10
```

<210> SEQ ID NO 12
<211> LENGTH: 7
<212> TYPE: PRT
<213> ORGANISM: artificial
<220> FEATURE:
<223> OTHER INFORMATION: antibody binding sequence

<400> SEQUENCE: 12

```
Ile Val Tyr Lys Pro Val Asp
1               5
```

<210> SEQ ID NO 13
<211> LENGTH: 314
<212> TYPE: PRT
<213> ORGANISM: artificial
<220> FEATURE:
<223> OTHER INFORMATION: cleavage product

<400> SEQUENCE: 13

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
```

```
            20                  25                  30
Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
            115                 120                 125

Ser Lys Ser Lys Asp Gly Thr Gly Ser Asp Asp Lys Lys Ala Lys Gly
            130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
            195                 200                 205

Arg Ser Arg Thr Pro Ser Leu Pro Thr Pro Pro Thr Arg Glu Pro Lys
            210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
            275                 280                 285

Ser Lys Cys Gly Ser Lys Asp Asn Ile Lys His Val Pro Gly Gly Gly
            290                 295                 300

Ser Val Gln Ile Val Tyr Lys Pro Val Asp
305                 310

<210> SEQ ID NO 14
<211> LENGTH: 285
<212> TYPE: PRT
<213> ORGANISM: artificial
<220> FEATURE:
<223> OTHER INFORMATION: TCP40 cleavage product

<400> SEQUENCE: 14

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
50                  55                  60

Asp Ala Lys Ser Thr Pro Thr Ala Glu Ala Glu Glu Ala Gly Ile Gly
```

```
            65                  70                  75                  80
Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys
                100                 105                 110

Ala Lys Gly Ala Asp Gly Lys Thr Lys Ile Ala Thr Pro Arg Gly Ala
            115                 120                 125

Ala Pro Pro Gly Gln Lys Gly Gln Ala Asn Ala Thr Arg Ile Pro Ala
        130                 135                 140

Lys Thr Pro Pro Ala Pro Lys Thr Pro Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Thr Arg
            180                 185                 190

Glu Pro Lys Lys Val Ala Val Val Arg Thr Pro Pro Lys Ser Pro Ser
        195                 200                 205

Ser Ala Lys Ser Arg Leu Gln Thr Ala Pro Val Pro Met Pro Asp Leu
    210                 215                 220

Lys Asn Val Lys Ser Lys Ile Gly Ser Thr Glu Asn Leu Lys His Gln
225                 230                 235                 240

Pro Gly Gly Gly Lys Val Gln Ile Ile Asn Lys Lys Leu Asp Leu Ser
                245                 250                 255

Asn Val Gln Ser Lys Cys Gly Ser Lys Asp Asn Ile Lys His Val Pro
            260                 265                 270

Gly Gly Gly Ser Val Gln Ile Val Tyr Lys Pro Val Asp
        275                 280                 285

<210> SEQ ID NO 15
<211> LENGTH: 283
<212> TYPE: PRT
<213> ORGANISM: artificial
<220> FEATURE:
<223> OTHER INFORMATION: TCP40 cleavage product

<400> SEQUENCE: 15

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
```

```
            145                 150                 155                 160
        Gly Gln Lys Gly Gln Ala Asn Ala Thr Arg Ile Pro Ala Lys Thr Pro
                        165                 170                 175

Pro Ala Pro Lys Thr Pro Pro Ser Ser Gly Glu Pro Lys Ser Gly
                        180                 185                 190

Asp Arg Ser Gly Tyr Ser Ser Pro Gly Ser Pro Gly Thr Pro Gly Ser
                        195                 200                 205

Arg Ser Arg Thr Pro Ser Leu Pro Thr Pro Thr Arg Glu Pro Lys
                        210                 215                 220

Lys Val Ala Val Val Arg Thr Pro Pro Lys Ser Pro Ser Ser Ala Lys
        225                 230                 235                 240

Ser Arg Leu Gln Thr Ala Pro Val Pro Met Pro Asp Leu Lys Asn Val
                        245                 250                 255

Lys Ser Lys Ile Gly Ser Thr Glu Asn Leu Lys His Gln Pro Gly Gly
                        260                 265                 270

Gly Lys Val Gln Ile Val Tyr Lys Pro Val Asp
                        275                 280

<210> SEQ ID NO 16
<211> LENGTH: 256
<212> TYPE: PRT
<213> ORGANISM: artificial
<220> FEATURE:
<223> OTHER INFORMATION: TCP35 cleavage product

<400> SEQUENCE: 16

Met Ala Glu Pro Arg Gln Glu Phe Glu Val Met Glu Asp His Ala Gly
        1               5                   10                  15

Thr Tyr Gly Leu Gly Asp Arg Lys Asp Gln Gly Gly Tyr Thr Met His
                        20                  25                  30

Gln Asp Gln Glu Gly Asp Thr Asp Ala Gly Leu Lys Ala Glu Glu Ala
                        35                  40                  45

Gly Ile Gly Asp Thr Pro Ser Leu Glu Asp Glu Ala Ala Gly His Val
                50                  55                  60

Thr Gln Ala Arg Met Val Ser Lys Ser Lys Asp Gly Thr Gly Ser Asp
        65                  70                  75                  80

Asp Lys Lys Ala Lys Gly Ala Asp Gly Lys Thr Lys Ile Ala Thr Pro
                        85                  90                  95

Arg Gly Ala Ala Pro Pro Gly Gln Lys Gly Gln Ala Asn Ala Thr Arg
                        100                 105                 110

Ile Pro Ala Lys Thr Pro Pro Ala Pro Lys Thr Pro Pro Ser Ser Gly
                        115                 120                 125

Glu Pro Pro Lys Ser Gly Asp Arg Ser Gly Tyr Ser Ser Pro Gly Ser
                        130                 135                 140

Pro Gly Thr Pro Gly Ser Arg Ser Arg Thr Pro Ser Leu Pro Thr Pro
        145                 150                 155                 160

Pro Thr Arg Glu Pro Lys Lys Val Ala Val Val Arg Thr Pro Pro Lys
                        165                 170                 175

Ser Pro Ser Ser Ala Lys Ser Arg Leu Gln Thr Ala Pro Val Pro Met
                        180                 185                 190

Pro Asp Leu Lys Asn Val Lys Ser Lys Ile Gly Ser Thr Glu Asn Leu
                        195                 200                 205

Lys His Gln Pro Gly Gly Gly Lys Val Gln Ile Ile Asn Lys Lys Leu
                        210                 215                 220

Asp Leu Ser Asn Val Gln Ser Lys Cys Gly Ser Lys Asp Asn Ile Lys
```

His Val Pro Gly Gly Gly Ser Val Gln Ile Val Tyr Lys Pro Val Asp
            245                 250                 255

<210> SEQ ID NO 17
<211> LENGTH: 254
<212> TYPE: PRT
<213> ORGANISM: artificial
<220> FEATURE:
<223> OTHER INFORMATION: TCP35 cleavage product

<400> SEQUENCE: 17

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Ala Glu Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys
            100                 105                 110

Ala Lys Gly Ala Asp Gly Lys Thr Lys Ile Ala Thr Pro Arg Gly Ala
        115                 120                 125

Ala Pro Pro Gly Gln Lys Gly Gln Ala Asn Ala Thr Arg Ile Pro Ala
    130                 135                 140

Lys Thr Pro Pro Ala Pro Lys Thr Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
            180                 185                 190

Glu Pro Lys Lys Val Ala Val Val Arg Thr Pro Pro Lys Ser Pro Ser
        195                 200                 205

Ser Ala Lys Ser Arg Leu Gln Thr Ala Pro Val Pro Met Pro Asp Leu
    210                 215                 220

Lys Asn Val Lys Ser Lys Ile Gly Ser Thr Glu Asn Leu Lys His Gln
225                 230                 235                 240

Pro Gly Gly Gly Lys Val Gln Ile Val Tyr Lys Pro Val Asp
                245                 250

<210> SEQ ID NO 18
<211> LENGTH: 225
<212> TYPE: PRT
<213> ORGANISM: artificial
<220> FEATURE:
<223> OTHER INFORMATION: TCP30 cleavage product

<400> SEQUENCE: 18

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

-continued

```
Gln Asp Gln Glu Gly Asp Thr Asp Ala Gly Leu Lys Ala Glu Glu Ala
                 35                  40                  45
Gly Ile Gly Asp Thr Pro Ser Leu Glu Asp Glu Ala Ala Gly His Val
         50                  55                  60
Thr Gln Ala Arg Met Val Ser Lys Ser Lys Asp Gly Thr Gly Ser Asp
 65                  70                  75                  80
Asp Lys Lys Ala Lys Gly Ala Asp Gly Lys Thr Lys Ile Ala Thr Pro
                 85                  90                  95
Arg Gly Ala Ala Pro Pro Gly Gln Lys Gly Gln Ala Asn Ala Thr Arg
            100                 105                 110
Ile Pro Ala Lys Thr Pro Pro Ala Pro Lys Thr Pro Pro Ser Ser Gly
            115                 120                 125
Glu Pro Pro Lys Ser Gly Asp Arg Ser Gly Tyr Ser Ser Pro Gly Ser
            130                 135                 140
Pro Gly Thr Pro Gly Ser Arg Ser Arg Thr Pro Ser Leu Pro Thr Pro
145                 150                 155                 160
Pro Thr Arg Glu Pro Lys Lys Val Ala Val Val Arg Thr Pro Pro Lys
                165                 170                 175
Ser Pro Ser Ser Ala Lys Ser Arg Leu Gln Thr Ala Pro Val Pro Met
            180                 185                 190
Pro Asp Leu Lys Asn Val Lys Ser Lys Ile Gly Ser Thr Glu Asn Leu
            195                 200                 205
Lys His Gln Pro Gly Gly Gly Lys Val Gln Ile Val Tyr Lys Pro Val
            210                 215                 220
Asp
225

<210> SEQ ID NO 19
<211> LENGTH: 5
<212> TYPE: PRT
<213> ORGANISM: artificial
<220> FEATURE:
<223> OTHER INFORMATION: caspase-2 inhibitor peptide
<220> FEATURE:
<221> NAME/KEY: MOD_RES
<222> LOCATION: (1)..(1)
<223> OTHER INFORMATION: METHYLATION
<220> FEATURE:
<221> NAME/KEY: MOD_RES
<222> LOCATION: (5)..(5)
<223> OTHER INFORMATION: ALDEHYDE GROUP

<400> SEQUENCE: 19

Tyr Lys Pro Val Asp
 1               5

<210> SEQ ID NO 20
<211> LENGTH: 5
<212> TYPE: PRT
<213> ORGANISM: artificial
<220> FEATURE:
<223> OTHER INFORMATION: caspase-2 inhibitor peptide
<220> FEATURE:
<221> NAME/KEY: MOD_RES
<222> LOCATION: (1)..(1)
<223> OTHER INFORMATION: METHYLATION
<220> FEATURE:
<221> NAME/KEY: MOD_RES
<222> LOCATION: (5)..(5)
<223> OTHER INFORMATION: ALDEHYDE GROUP

<400> SEQUENCE: 20

Tyr Asp Pro Val Asp
```

```
1               5

<210> SEQ ID NO 21
<211> LENGTH: 5
<212> TYPE: PRT
<213> ORGANISM: artificial
<220> FEATURE:
<223> OTHER INFORMATION: caspase-2 inhibitor peptide
<220> FEATURE:
<221> NAME/KEY: MOD_RES
<222> LOCATION: (1)..(1)
<223> OTHER INFORMATION: METHYLATION
<220> FEATURE:
<221> NAME/KEY: MOD_RES
<222> LOCATION: (5)..(5)
<223> OTHER INFORMATION: ALDEHYDE GROUP

<400> SEQUENCE: 21

Tyr Ser Pro Val Asp
1               5

<210> SEQ ID NO 22
<211> LENGTH: 5
<212> TYPE: PRT
<213> ORGANISM: artificial
<220> FEATURE:
<223> OTHER INFORMATION: caspase-2 inhibitor peptide
<220> FEATURE:
<221> NAME/KEY: MOD_RES
<222> LOCATION: (1)..(1)
<223> OTHER INFORMATION: METHYLATION
<220> FEATURE:
<221> NAME/KEY: MOD_RES
<222> LOCATION: (5)..(5)
<223> OTHER INFORMATION: ALDEHYDE GROUP

<400> SEQUENCE: 22

Tyr Cys Pro Val Asp
1               5

<210> SEQ ID NO 23
<211> LENGTH: 5
<212> TYPE: PRT
<213> ORGANISM: artificial
<220> FEATURE:
<223> OTHER INFORMATION: caspase-2 inhibitor peptide
<220> FEATURE:
<221> NAME/KEY: MOD_RES
<222> LOCATION: (1)..(1)
<223> OTHER INFORMATION: METHYLATION
<220> FEATURE:
<221> NAME/KEY: MOD_RES
<222> LOCATION: (5)..(5)
<223> OTHER INFORMATION: ALDEHYDE GROUP

<400> SEQUENCE: 23

Phe Lys Pro Val Asp
1               5

<210> SEQ ID NO 24
<211> LENGTH: 5
<212> TYPE: PRT
<213> ORGANISM: artificial
<220> FEATURE:
<223> OTHER INFORMATION: caspase-2 inhibitor peptide
<220> FEATURE:
<221> NAME/KEY: MOD_RES
<222> LOCATION: (1)..(1)
<223> OTHER INFORMATION: F at position 1 is a 4-fluorophenylalanine
<220> FEATURE:
<221> NAME/KEY: MOD_RES
<222> LOCATION: (1)..(1)
```

```
<223> OTHER INFORMATION: METHYLATION
<220> FEATURE:
<221> NAME/KEY: MOD_RES
<222> LOCATION: (5)..(5)
<223> OTHER INFORMATION: ALDEHYDE GROUP

<400> SEQUENCE: 24

Phe Lys Pro Val Asp
1               5

<210> SEQ ID NO 25
<211> LENGTH: 5
<212> TYPE: PRT
<213> ORGANISM: artificial
<220> FEATURE:
<223> OTHER INFORMATION: caspase-2 inhibitor peptide
<220> FEATURE:
<221> NAME/KEY: MOD_RES
<222> LOCATION: (1)..(1)
<223> OTHER INFORMATION: BENZYL GROUP
<220> FEATURE:
<221> NAME/KEY: MOD_RES
<222> LOCATION: (5)..(5)
<223> OTHER INFORMATION: ALDEHYDE GROUP

<400> SEQUENCE: 25

Tyr Lys Pro Val Asp
1               5

<210> SEQ ID NO 26
<211> LENGTH: 5
<212> TYPE: PRT
<213> ORGANISM: artificial
<220> FEATURE:
<223> OTHER INFORMATION: caspase-2 inhibitor peptide
<220> FEATURE:
<221> NAME/KEY: MOD_RES
<222> LOCATION: (1)..(1)
<223> OTHER INFORMATION: BENZYL GROUP
<220> FEATURE:
<221> NAME/KEY: MOD_RES
<222> LOCATION: (5)..(5)
<223> OTHER INFORMATION: ALDEHYDE GROUP

<400> SEQUENCE: 26

Tyr Asp Pro Val Asp
1               5

<210> SEQ ID NO 27
<211> LENGTH: 5
<212> TYPE: PRT
<213> ORGANISM: artificial
<220> FEATURE:
<223> OTHER INFORMATION: caspase-2 inhibitor peptide
<220> FEATURE:
<221> NAME/KEY: MOD_RES
<222> LOCATION: (1)..(1)
<223> OTHER INFORMATION: METHYLATION
<220> FEATURE:
<221> NAME/KEY: MOD_RES
<222> LOCATION: (5)..(5)
<223> OTHER INFORMATION: ALDEHYDE GROUP

<400> SEQUENCE: 27

Tyr Lys Pro Phe Asp
1               5

<210> SEQ ID NO 28
<211> LENGTH: 5
<212> TYPE: PRT
<213> ORGANISM: artificial
```

-continued

```
<220> FEATURE:
<223> OTHER INFORMATION: caspase-2 inhibitor peptide
<220> FEATURE:
<221> NAME/KEY: MOD_RES
<222> LOCATION: (1)..(1)
<223> OTHER INFORMATION: METHYLATION
<220> FEATURE:
<221> NAME/KEY: MOD_RES
<222> LOCATION: (5)..(5)
<223> OTHER INFORMATION: ALDEHYDE GROUP

<400> SEQUENCE: 28

Tyr Asp Pro Phe Asp
1               5

<210> SEQ ID NO 29
<211> LENGTH: 5
<212> TYPE: PRT
<213> ORGANISM: artificial
<220> FEATURE:
<223> OTHER INFORMATION: caspase-2 inhibitor peptide
<220> FEATURE:
<221> NAME/KEY: MOD_RES
<222> LOCATION: (1)..(1)
<223> OTHER INFORMATION: METHYLATION
<220> FEATURE:
<221> NAME/KEY: MOD_RES
<222> LOCATION: (5)..(5)
<223> OTHER INFORMATION: ALDEHYDE GROUP

<400> SEQUENCE: 29

Tyr Lys Pro Ala Asp
1               5

<210> SEQ ID NO 30
<211> LENGTH: 5
<212> TYPE: PRT
<213> ORGANISM: artificial
<220> FEATURE:
<223> OTHER INFORMATION: caspase-2 inhibitor peptide
<220> FEATURE:
<221> NAME/KEY: MOD_RES
<222> LOCATION: (1)..(1)
<223> OTHER INFORMATION: METHYLATION
<220> FEATURE:
<221> NAME/KEY: MOD_RES
<222> LOCATION: (5)..(5)
<223> OTHER INFORMATION: ALDEHYDE GROUP

<400> SEQUENCE: 30

Tyr Asp Pro Ala Asp
1               5

<210> SEQ ID NO 31
<211> LENGTH: 5
<212> TYPE: PRT
<213> ORGANISM: artificial
<220> FEATURE:
<223> OTHER INFORMATION: caspase-2 inhibitor peptide
<220> FEATURE:
<221> NAME/KEY: MOD_RES
<222> LOCATION: (1)..(1)
<223> OTHER INFORMATION: METHYLATION
<220> FEATURE:
<221> NAME/KEY: MOD_RES
<222> LOCATION: (5)..(5)
<223> OTHER INFORMATION: ALDEHYDE GROUP

<400> SEQUENCE: 31

Tyr Lys Val Val Asp
1               5
```

```
<210> SEQ ID NO 32
<211> LENGTH: 5
<212> TYPE: PRT
<213> ORGANISM: artificial
<220> FEATURE:
<223> OTHER INFORMATION: caspase-2 inhibitor peptide
<220> FEATURE:
<221> NAME/KEY: MOD_RES
<222> LOCATION: (1)..(1)
<223> OTHER INFORMATION: METHYLATION
<220> FEATURE:
<221> NAME/KEY: MOD_RES
<222> LOCATION: (5)..(5)
<223> OTHER INFORMATION: ALDEHYDE GROUP

<400> SEQUENCE: 32

Tyr Asp Val Val Asp
1               5

<210> SEQ ID NO 33
<211> LENGTH: 5
<212> TYPE: PRT
<213> ORGANISM: artificial
<220> FEATURE:
<223> OTHER INFORMATION: caspase-2 inhibitor peptide
<220> FEATURE:
<221> NAME/KEY: MOD_RES
<222> LOCATION: (1)..(1)
<223> OTHER INFORMATION: METHYLATION
<220> FEATURE:
<221> NAME/KEY: MOD_RES
<222> LOCATION: (5)..(5)
<223> OTHER INFORMATION: ALDEHYDE GROUP

<400> SEQUENCE: 33

Tyr Lys Pro Tyr Asp
1               5

<210> SEQ ID NO 34
<211> LENGTH: 5
<212> TYPE: PRT
<213> ORGANISM: artificial
<220> FEATURE:
<223> OTHER INFORMATION: caspase-2 inhibitor peptide
<220> FEATURE:
<221> NAME/KEY: MOD_RES
<222> LOCATION: (1)..(1)
<223> OTHER INFORMATION: METHYLATION
<220> FEATURE:
<221> NAME/KEY: MOD_RES
<222> LOCATION: (5)..(5)
<223> OTHER INFORMATION: ALDEHYDE GROUP

<400> SEQUENCE: 34

Tyr Lys Pro Val Asp
1               5

<210> SEQ ID NO 35
<211> LENGTH: 5
<212> TYPE: PRT
<213> ORGANISM: artificial
<220> FEATURE:
<223> OTHER INFORMATION: canonical caspase-2 cleavage sequence

<400> SEQUENCE: 35

Val Asp Val Ala Asp
1               5

<210> SEQ ID NO 36
<211> LENGTH: 5
```

-continued

```
<212> TYPE: PRT
<213> ORGANISM: artificial
<220> FEATURE:
<223> OTHER INFORMATION: caspase-2 inhibitor sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (5)..(5)
<223> OTHER INFORMATION: ALDEHYDE GROUP

<400> SEQUENCE: 36

Val Asp Val Ala Asp
1               5

<210> SEQ ID NO 37
<211> LENGTH: 4
<212> TYPE: PRT
<213> ORGANISM: artificial
<220> FEATURE:
<223> OTHER INFORMATION: caspase-2 inhibitor sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: ALDEHYDE GROUP

<400> SEQUENCE: 37

Asp Glu Val Asp
1

<210> SEQ ID NO 38
<211> LENGTH: 5
<212> TYPE: PRT
<213> ORGANISM: artificial
<220> FEATURE:
<223> OTHER INFORMATION: caspase-2 inhibitor consensus sequence
<220> FEATURE:
<221> NAME/KEY: MISC_FEATURE
<222> LOCATION: (1)..(1)
<223> OTHER INFORMATION: X at position 1 is tyrosine of phenylalanine
<220> FEATURE:
<221> NAME/KEY: MISC_FEATURE
<222> LOCATION: (2)..(2)
<223> OTHER INFORMATION: X at position 2 is lysine, aspartic acid,
      serine, or cysteine
<220> FEATURE:
<221> NAME/KEY: MISC_FEATURE
<222> LOCATION: (3)..(3)
<223> OTHER INFORMATION: X at position 3 is proline or valine
<220> FEATURE:
<221> NAME/KEY: MISC_FEATURE
<222> LOCATION: (4)..(4)
<223> OTHER INFORMATION: X at position 4 is valine, phenylalanine,
      alanine, or tyrosine

<400> SEQUENCE: 38

Xaa Xaa Xaa Xaa Asp
1               5
```

COMPOSITIONS AND METHODS RELATED TO TAUOPATHY

CROSS-REFERENCE TO RELATED APPLICATION

This application claims priority to U.S. Provisional Patent Application Ser. No. 61/738,510, filed Dec. 18, 2012, which is incorporated herein by reference.

GOVERNMENT FUNDING

This invention was made with government support under R01-NS063214 awarded by the National Institutes of Health. The government has certain rights in the invention.

SEQUENCE LISTING

This application contains a Sequence Listing electronically submitted to the United States Patent and Trademark Office via EFS-Web as an ASCII text file entitled "110-03950101_SequenceListing_ST25.txt" having a size of 25 kilobytes and created on Dec. 16, 2013. The information contained in the Sequence Listing is incorporated by reference herein.

BACKGROUND

Alzheimer's disease is characterized by the accumulation of amyloid plaques, composed of $A\beta$ proteins, and neurofibrillary tangles, composed of tau proteins. It can be genetically linked to mutations that increase the propensity for $A\beta$ to form pathogenic aggregates; interestingly, however, it is never linked to mutations in tau. An implication of this genetic dichotomy is that the formation of a pathogenic form of $A\beta$, but not tau, initiates Alzheimer's disease. $A\beta*56$ (Abeta star 56) has been proposed to be the pathogenic form of $A\beta$ that initiates Alzheimer's disease.

$A\beta*56$ requires tau to impair memory function. Tau is therefore an $A\beta$ effector molecule. The clinical observation that amyloid plaques deposit prior to abnormal increases in spinal fluid tau is consistent with this idea. These and other related results indicate that the pathogenesis of Alzheimer's disease requires both the $A\beta$ and tau proteins.

SUMMARY OF THE INVENTION

In one aspect, this disclosure provides an isolated polypeptide that includes a core pentapeptide, with the proviso that the isolated polypeptide is not a native full-length tau protein. In some embodiments, the isolated polypeptide of claim 1 further comprising at least one amino acid appended to the N-terminus of the core pentapeptide. In other embodiments, the isolated polypeptide of either claim 1 or claim 2 further comprising at least one amino acid appended to the C-terminus of the core pentapeptide. In some embodiments, the isolated polypeptide can be a peptidomimetic of the isolated polypeptide of any preceding embodiment.

In some embodiments, the core pentapeptide can be SEQ ID NO:1.

In another aspect, this disclosure provides a composition that includes the isolated polypeptide of any preceding embodiments and a pharmaceutically acceptable carrier.

In another aspect, this disclosure provides a method that generally includes administering to a subject a composition that includes an isolated polypeptide of any embodiment described above. In some cases, the method can involve administering to a subject having or at risk of having a tauopathy an amount of the composition effective to inhibit at least one of the following: caspase-2-dependent cleavage of tau, production of TCP30, production of TCP35, or production of TCP40. In other cases, the method can involve administering to a subject having a tauopathy an amount of the composition effective to ameliorate at least one clinical sign or symptom characteristic of a tauopathic condition. In still other cases, the method can involve administering to a subject at risk of having a tauopathy an amount of the composition effective to protect the subject against development of a tauopathic condition.

In some embodiments, the tauopathic condition can include Alzheimer's disease.

In another aspect, this disclosure provides methods of screening compounds. In some embodiments, the method can include providing a mixture of caspase-2, a test compound, and a labeled caspase-2 cleavage substrate; incubating the mixture under conditions effective for caspase-2 to cleave the caspase-2 cleavage substrate in the absence of the test compound to produce a labeled caspase-2 cleavage product; detecting at least one of: the uncleaved labeled caspase-2 cleavage substrate or the labeled caspase-2 cleavage product; and identifying the test compound as an inhibitor of caspase-2 if at least one of the following is true: the uncleaved labeled caspase-2 cleavage substrate is detected in an amount greater than a first predetermined reference value, or the labeled caspase-2 cleavage product is detected in an amount less than a second predetermined reference value. In other embodiments, the method can include providing a mixture of a labeled caspase-2 cleavage substrate, a labeled caspase-2 cleavage product in a predetermined ratio to the caspase-2 cleavage substrate, caspase-2, a test compound; incubating the mixture under conditions effective for caspase-2 to cleave the caspase-2 cleavage substrate in the absence of the test compound to produce the labeled caspase-2 cleavage product; determining the ratio of the caspase-2 cleavage substrate to the caspase-2 cleavage product; and identifying the test compound as an inhibitor of caspase-2 if the ratio of caspase-2 cleavage product:caspase-2 cleavage substrate is less than a reference ratio of caspase-2 cleavage product:caspase-2 cleavage substrate in the absence of the test compound.

In some cases of either embodiment of the screening methods, the labeled caspase-2 cleavage substrate comprises SEQ ID NO:2 and/or the caspase-2 cleavage product comprises SEQ ID NO:3. In other cases of either embodiment of the screening methods, the labeled caspase-2 cleavage substrate comprises SEQ ID NO:4 and/or the caspase-2 cleavage product comprises SEQ ID NO:5.

In another aspect, this disclosure provides an antibody preparation that includes antibody that specifically binds to SEQ ID NO:10. In some embodiments, the antibody can include polyclonal antibody. In other embodiments, the antibody can include a monoclonal antibody.

In another aspect, this disclosure provides a method that generally includes contacting a biological sample fluid from a subject that includes cerebrospinal with an antibody preparation that includes antibody that specifically binds to SEQ ID NO:10 and detecting a ligand in the sample that specifically binds the antibody preparation. In some embodiments, the ligand can include the amino acid sequence of SEQ ID NO:10. In some embodiments, the subject may exhibit at least one symptom or clinical sign of a tauopathic condition. In other embodiments, the subject need not exhibit at least one symptom or clinical sign of a tauopathic condition.

In another aspect, this disclosure provides an aptamer preparation that includes one or more aptamers that specifically bind to SEQ ID NO:10.

In yet another aspect, this disclosure provides a method that generally includes contacting a biological sample from a subject with an aptamer preparation that includes one or more aptamers that specifically bind to SEQ ID NO: 10. In some embodiments, the biological sample can includes cerebral spinal fluid.

The above summary is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 2. The expression of TCP35 parallels the development of cognitive impairment. The western blot panels (A) show full length tau (55 kDa) and TCP35 in the hippocampus of rTg4510 mice from 1.3 to 4.5 months of age (probed with antibody Tau-5 recognizing mouse and human tau). Panels B and C show the quantification of age-dependent TCP35 expression (B, densitometry) and the development of memory impairment (C, percent time in the target quadrant).

FIG. 18. (A) Design of pentapeptide inhibitors of caspase-2 (cleavage sequence SEQ ID NO:1 and canonical sequence SEQ ID NO:35). (B) Generalized structure of pentapeptide inhibitors of caspase-2, where with $R_1$=Ac, $aa_x$=side chains of naturally-occurring D-amino-acids or L-amino-acids, and $R_2$=a group that covalently links to the caspase active site cysteine. (C) Exemplary chemical groups that covalently link to the caspase active site cysteine.

FIG. 19. (A) Generalized structure of peptidomimetics related to the originally-designed pentapeptide inhibitor of caspase-2, where $R_1$=acetyl, acyl, aryl, heteroaryl, diaryl, biaryl, aralkyl, variously substituted; $aa_x$=D- or L-amino-acids, or unnatural amino acids. $aa_1$ can be replaced as reflected in (B), where $R_5$ is COOH, COR, $CO_2R$, CN, $OCO_2R$, $NO_2$, NCOR, SCOR, SOR, $SO_2R$, $NHSO_2R$, NHCOR, or tetrazole; X is peptidic carbamoyl group, i.e., —CONH—, can be replaced by peptidomimetic bonds such as —$CH_2NH$—, —$COCH_2$—, —CSNH—, and retro-inverso bonds or oxazole, imidazole and thiophene, variously substituted; and $R_2$ is as shown in (C) or can be acetyl, acyl, aryl, heteroaryl, diaryl, biaryl, aralkyl variously substituted.

DETAILED DESCRIPTION OF ILLUSTRATIVE EMBODIMENTS

Figure 1:
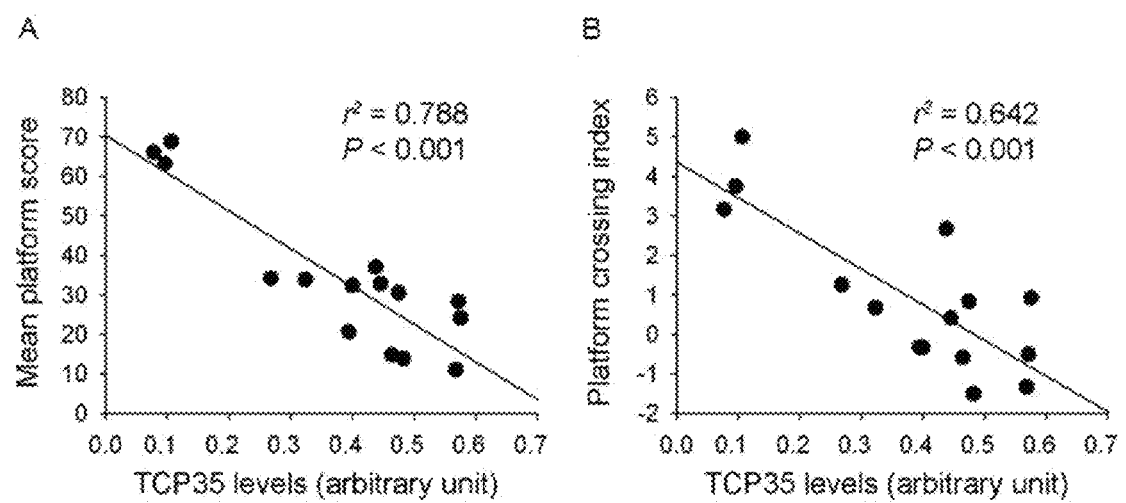
FIG. 1. Inverse correlation between memory function and TCP35 levels. Spatial reference memory of 6-month (M) rTg510 mice in which tau expression was suppressed by doxycycline until they were 3M was assessed using the Morris water maze assay. Mice were then killed and TCP35 levels in total forebrain homogenates were measured by immunoblotting. (A) Mean platform score and (B) platform crossing index correlated inversely with TCP35 levels. Mean platform score is the average %-time of four probe trials. Platform crossing index is the number of target platform crossings minus the average number of non-target platform crossings.

Although a great deal is known about the neuropathology of tauopathy, much less is understood about the molecular processes that cause the clinical symptoms. Consequently, nearly all research to develop new treatments for Alzheimer's disease has been directed at ameliorating the effects of neuronal loss and reducing neuropathology. This has led to the development of medications that temporarily improve symptoms and/or clinical signs of the disease but do not address the underlying cause of the disease.

Much research on tau still aims to understand how it kills neurons and how it aggregates to form neurofibrillary tangles. In contrast, the work described herein addresses the deterioration in brain function that takes place before neuron loss occurs and is unrelated to neurofibrillary tangles, by specifically addressing the basic question of the form of tau (here called tau*) initiates memory loss in tauopathy.

As noted in the background, the pathogenesis of Alzheimer's disease requires both the Aβ and tau proteins. We have determined that specific forms of Aβ and tau proteins are involved. For example, Aβ*56 can initiate the disease long before the degenerative processes progress to the point of diagnostic certainty, and tau* (tau star) causes the clinical symptoms of Alzheimer's disease that are not due to neuronal loss. We have, therefore, investigated tau*, the molecular species of tau involved in initiating the clinical symptoms of tauopathy. We report identifying tau* and a potential molecular mechanism leading to its formation.

We identify markers that have not been previously implicated in the pathogenesis of Alzheimer's disease or other tauopathy. The markers are generated when caspase-2 cleaves various isoforms of tau at aspartate 314 (D314). One marker, TCP35, has an approximate molecular weight of 35 kDa. TCP30 has an apparent molecular weight of 30 kDa. TCP40 has an apparent molecular weight of 40 kDa. Caspase-2, while involved in Aβ-related neurotoxicity, has not been associated with tau-related neural dysfunction. Moreover, we have identified the cleavage site at which caspase-2 cleaves tau, designed an inhibitor of caspase-2-dependent tau cleavage that may have therapeutic potential, and designed high throughput assays for the identification of additional inhibitors of caspase-2-dependent tau cleavage.

Thus, in one aspect, this disclosure provides a composition that includes an isolated polypeptide that comprises an amino acid sequence designed to interfere with caspase-2-dependent tau cleavage. As used herein, "isolated" and variations thereof refer to a polypeptide that has been removed from its natural environment to any degree. For instance, an isolated polypeptide is a polypeptide that has been removed from the cytoplasm and/or any membrane of a cell, and many of the polypeptides, nucleic acids, and other cellular material of its natural environment are no longer present. As such chemically synthesized polypeptides are, by definitions, removed from their natural environment and, therefore, "isolated." The term "isolated" does not convey any specific degree to which the other cellular components are removed. As used herein, "polypeptide" refers to a sequence of amino acid residues without regard to the length of the sequence, regardless of whether each amino acid residue in the sequence is bound to its neighbor through a peptide bond. Therefore, the term "polypeptide" refers to any amino acid sequence having at least two amino acids and includes peptidomimetics.

The initial design of inhibitors of caspase-2 dependent tau cleavage involved sequential changes of the amino acids in the cleavage sequence and leading to the canonical cleavage sequence reported in the literature. This allows the generation of novel linear, reversible, covalent, pentapeptide inhibitors. In some embodiments, however, the pentapeptide inhibitors may be designed to include a group that interacts with, for example, the cysteine residue at the caspase-2 active site in a noncovalent manner. The "canonical cleavage sequence" is the sequence of five amino acids (VDVAD, SEQ ID NO:35) that have been identified to constitute the most potent inhibitor of caspase-2, when the pentapeptide has the formula VDVAD-X, where X is a chemical group that covalently links to the caspase active site cysteine (FIG. 18B). In some embodiments, X can include, for example, any one of the groups illustrated in FIG. 18C.

Thus, in some embodiments, the isolated polypeptide can be any polypeptide that possesses the structure illustrated in FIG. 18.

A designed inhibitor can include one or more further modifications that can provide metabolic stability and/or cell permeability.

Table 1 lists exemplary pentapeptides that have been designed and synthesized based on the general structure:

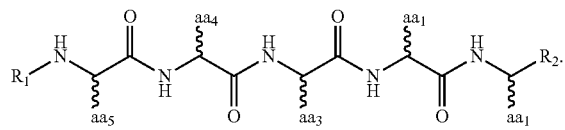

In competitive binding assays against caspase-2, caspase-3, caspase-6, and caspase-7 (PROMEGA-GLO 2; Promega, Corp., Madison, Wis.), the parent pentapeptide based on the sequence Ac-YKPVD-CHO (SEQ ID NO: 1) exhibited a $K_i$ value of 200 nM (caspase-2), 19.8 μM (caspase-3), 184 μM (caspase-6) and greater than 100 μM (caspase-7). The alternative pentapeptides reflected in Table 1 exhibit similar activity.

TABLE 1

| $R_1$ | $aa_5$ | $aa_4$ | $aa_3$ | $aa_2$ | $aa_1$ | $R_2$ | SEQ ID NO | MW (Da) | cLogP |
|---|---|---|---|---|---|---|---|---|---|
| CH₃ | Y | K | P | V | D | CHO | 1 | 646.7 | −2.51 |
| CH₃ | Y | K(Ac) | P | V | D | CHO | 19 | 688.8 | −2.58 |
| CH₃ | Y | D | P | V | D | CHO | 20 | 633.7 | −3.03 |
| CH₃ | Y | S | P | V | D | CHO | 21 | 605.6 | −3.10 |
| CH₃ | Y | C | P | V | D | CHO | 22 | 621.7 | −2.28 |
| CH₃ | F | K | P | V | D | CHO | 23 | 630.7 | −2.12 |
| CH₃ | 4F—F | K | P | V | D | CHO | 24 | 648.7 | −1.96 |
| benzyl | Y | K | P | V | D | CHO | 25 | 722.8 | −1.47 |
| benzyl | Y | D | P | V | D | CHO | 26 | 709.7 | −1.75 |
| CH₃ | Y | K | P | F | D | CHO | 27 | 694.8 | −1.72 |
| CH₃ | Y | D | P | F | D | CHO | 28 | 681.7 | −2.24 |
| CH₃ | Y | K | P | A | D | CHO | 29 | 618.7 | −3.39 |
| CH₃ | Y | D | P | A | D | CHO | 30 | 605.6 | −3.91 |
| CH₃ | Y | K | V | V | D | CHO | 31 | 648.8 | −1.84 |
| CH₃ | Y | D | V | V | D | CHO | 32 | 635.7 | −2.36 |
| CH₃ | Y | K | P | Y | D | CHO | 33 | 710.8 | −2.11 |
| CH₃ | Y | K | P | V | D | CHO | 34 | 697.7 | −2.63 |

4F-F: 4-fluorophenylalanine

Thus, in one particular embodiment, the isolated polypeptide can include the amino acids Tyr-Lys-Pro-Val-Asp (SEQ ID NO:1). In other particular embodiments, the isolated polypeptide can include the amino acids of any one or more of SEQ ID NO:19, SEQ ID NO:20, SEQ ID NO:21, SEQ ID NO:22, SEQ ID NO:23, SEQ ID NO: 24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, or SEQ ID NO:34.

The amino acid sequences of the pentapeptides reflected in Table 1 (SEQ ID NO:1, SEQ ID NO:19, SEQ ID NO:20, SEQ ID NO:21, SEQ ID NO:22, SEQ ID NO:23, SEQ ID NO: 24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, and SEQ ID NO:34) were designed to mimic, at least in part, the site at which caspase-2 cleaves tau. In so doing, the polypeptides can inhibit caspase-2-dependent cleavage of tau and the resulting production of TCP30, TCP35, and/or TCP40. As used herein, "inhibit" and variations thereof refer to any measurable reduction of caspase-2-dependent cleavage of tau and/or any measurable reduction in the presence of TCP30, TCP35, and/or TCP40 (collectively herein for brevity, "caspase-2 tau cleavage"). The extent of inhibition may be characterized as a percentage of a normal level of activity. Without wishing to be bound by any particular theory, the isolated polypeptide can occupy the active site of caspase-2. In some cases, the polypeptide may serve as a competitive inhibitor of caspase-2 tau cleavage.

In some embodiments, the isolated polypeptide may be variant of a pentapeptide reflected in Table 1 that includes one or more additional amino acids appended to either terminus of core pentapeptide (e.g., SEQ ID NO:1, SEQ ID NO:19, SEQ ID NO:20, SEQ ID NO:21, SEQ ID NO:22, SEQ ID NO:23, SEQ ID NO: 24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, or SEQ ID NO:34) so long as the variant polypeptide retains the ability to inhibit caspase-2 tau cleavage. Molecular modeling algorithms make it routine for one to determine whether any particular variant of a core pentapeptide will adopt a conformation that will allow the variant to inhibit caspase-2 tau cleavage. Thus, the isolated polypeptide can include an addition of, for example, 1, 2, 3, 4, 5, 6, 7, 8, 9, 10, 11, 12, 13, 14, 15, 16, 17, 18, 19, or 20 amino acid residues appended to either terminus of a core pentapeptide. In certain embodiments, the isolated polypeptide can include an addition of, for example, no more than 10 amino acid residues to either terminus of a core pentapeptide. In embodiments in which the isolated polypeptide includes an addition to each terminus of a core pentapeptide, the length and/or the particular amino acid sequence added to one terminus may be independent of the length and/or particular amino acid sequence added to the other terminus.

In some embodiments, the isolated polypeptide also may be a variant of a core pentapeptide that includes one or more conservative substitutions so long as the variant polypeptide retains the ability to inhibit caspase-2 tau cleavage. A conservative substitution for an amino acid in the isolated polypeptide may be selected from other members of the class to which the amino acid belongs. For example, it is well-known in the art of protein biochemistry that an amino acid belonging to a grouping of amino acids having a particular size or characteristic (such as charge, hydrophobicity and hydrophilicity) can be substituted for another amino acid without altering the activity of a protein. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Conservative substitutions include, for example, Lys for Arg and vice versa to maintain a positive charge; Glu for Asp and vice versa to maintain a negative charge; Ser for Thr so that a free —OH is maintained; and Gln for Asn to maintain a free —NH₂.

In some embodiments, the isolated polypeptide also can be designed to provide additional sequences, such as, for example, the addition of coding sequences for added C-terminal or N-terminal amino acids that may facilitate purification by trapping on columns or use of antibodies. Such tags include, for example, histidine-rich tags that allow purification of polypeptides on nickel columns. Such gene modification techniques and suitable additional sequences are well known in the molecular biology arts.

In some embodiments, the isolated polypeptide can include one or more post-expression biological or chemical modifications of the polypeptide such as for example, a glycosylation, an acetylation, a phosphorylation, and the like, or any combination of two or more such modifications.

In some embodiments, the isolated polypeptide can be modified to include a chemical group that can covalently or non-covalently bind to the cysteine residue at the caspase-2 active site. For example, the isolated polypeptide can include certain amino acid derivatives that can induce inhibitory interactions with caspases. For example, a core pentapeptide reflected in Table 1, or the polypeptides with conservative amino acid substitutions as describe above, can be modified to be peptide-Asp*, where Asp* can include a terminal modification reflected in, for example, the modifications shown as $R_2$ in FIGS. 18C and 19C. $R_2$ can be as shown in FIG. 18C or FIG. 19C or can be an acetyl group, an acyl group, an aryl group, a heteroaryl group, a diaryl group, a biaryl group, or an aralkyl group, any of which may be variously substituted In the context of $R_2$, "variously substituted" means that there may be one or more substituent group present on that specified moiety. Exemplary substituent groups include, for example, fluorine (F), chlorine (Cl), bromine (Br), trifluoromethyl ($CF_3$), alkyl, hydroxy (OH), alkoxy (OR), alkylthio (SR), cyano, carboxyl ester ($CO_2R$), amino ($NH_2$) or amido (NHCOR).

In some embodiments, the isolated polypeptide may be modified to include a chemical group reflected as $R_1$ in FIG. 18B or FIG. 19A. $R_1$ can be modified to include an acetyl group, an acyl group, an aryl group, a heteroaryl group, a diaryl group, a biaryl group, or an aralkyl group, any of which may be variously substituted. In the context of $R_1$, "variously substituted" means that there may be one or more substituent group present on that specified moiety such as fluorine (F), chlorine (Cl), bromine (Br), trifluoromethyl ($CF_3$), alkyl, hydroxy (OH), alkoxy (OR), alkylthio (SR), cyano, carboxyl ester ($CO_2R$), amino ($NH_2$) or amido (NHCOR).

Amino acids $aa_1$-$aa_5$ can be any D-amino acid, L-aminoacid, or unnatural amino acid such as, for example, a pseudopeptide, a dipepsipeptide, or a β3-aza aminoacid. More generally, an unnatural amino acids can also describe a bioisoteric replacement of the lateral chain of natural amino acids such as, for example, pyridinyl-, naphthyl-, homophenyl-, thienyl-, quinolyl-, pyrimidyl-alanine for phenylalanine; tyrosine or tryptophan amino acid instead of tyrosine; nor-leucine, cycloalkyl-alanine, cylohexyl glycine, spirocyloalkyl glycine for leucine, isoleucine, valine, alanine; piperazinyl-alanine for lysine; thiaproline, 3- and 4-fluoro-, alkoxy-, aryloxy, alkylthio-, amino-proline for proline.

In some embodiments, $aa_1$ can be replaced as reflected in FIG. 19B, where $R_5$ is COOH, COR, $CO_2R$, CN, $OCO_2R$, $NO_2$, NCOR, SCOR, SOR, $SO_2R$, $NHSO_2R$, NHCOR, or tetrazole; X is peptidic carbamoyl group, i.e., —CONH—, can be replaced by peptidomimetic bonds such as, for example, —$CH_2NH$—, —$COCH_2$, —CSNH—, and retro-inverso bonds or oxazole, imidazole and thiophene, any of which can be variously substituted. Exemplary substituents can include, for example, fluorine (F), chlorine (Cl), bromine (Br), trifluoromethyl ($CF_3$), alkyl, hydroxy (OH), alkoxy (OR), alkylthio (SR), cyano, carboxyl ester ($CO_2R$), amino ($NH_2$) or amido (NHCOR)).

Additionally, some embodiments of the isolated polypeptide can include any combination of two or more features of the various embodiments described above. Moreover, the site of any of the modifications described above may be to one or more of the amino acid residues of a core pentapeptide or, in some cases, to amino acids residues that are part of an addition to either the C-terminus or the N-terminus of a core pentapeptide.

In some embodiments, the isolated polypeptide can include a prodrug modification. As used herein, a "prodrug modification" refers to a derivative of an isolated polypeptide as described herein that can undergo a chemical or enzymatic biotransformation, thereby releasing the active isolated polypeptide in the body. Various conventional prodrug modifications are known in the pharmaceutical arts.

In some embodiments, the isolated polypeptide may be a peptidomimetic. As used herein, the term "peptidomimetic" refers to a polypeptide designed to mimic a template polypeptide, but includes at least one non-naturally occurring modification that results is in conferring a favorable characteristic to the peptidomimetic. Various conventional modifications of this sort—e.g., such as linking of amino acid side chains, substitution of atoms in the peptide backbone, the replacement of amino acids with aromatic rings or heteroaromatic rings, substituting a D-amino acid residue for an L-amino acids residues, or substituting a non-peptide linkage for a peptide linkage between adjacent amino acid residues—are known in the pharmaceutical arts. Exemplary non-peptide linkages include, for example, —$CH_2NH$—, —$CH_2S$—, —$CH_2$—$CH_2$—, —CH=CH— (cis and trans), —$COCH_2$—, —$CH(OH)CH_2$—, or —$CH_2SO$—. A peptidomimetic may possess one or more advantages over a natural polypeptide including, for example, more economical production, greater chemical stability, altered specificity, or enhanced pharmacological properties such as half-life, absorption, potency, or efficacy.

In another aspect, this disclosure provides compositions that include the isolated polypeptide described above. Any embodiment of the isolated polypeptide may be a component of such a composition.

The composition described herein can include a "pharmaceutically acceptable carrier." As used herein, "carrier" includes any solvent, dispersion medium, vehicle, coating, diluent, antibacterial, and/or antifungal agent, isotonic agent, absorption delaying agent, buffer, carrier solution, suspension, colloid, and the like. The use of such media and/or agents for pharmaceutical active substances is well known in the art. Except insofar as any conventional media or agent is incompatible with the isolated polypeptide, its use in the therapeutic compositions is contemplated. Supplementary active ingredients also can be incorporated into the compositions. As used herein, "pharmaceutically acceptable" refers to a material that is not biologically or otherwise undesirable, i.e., the material may be administered to an individual along with the isolated polypeptide without causing any undesirable biological effects or interacting in a deleterious manner with any of the other components of the pharmaceutical composition in which it is contained.

A pharmaceutical composition that includes the isolated polypeptide may be prepared as any suitable pharmaceutical formulation. The pharmaceutical formulation may be any suitable form adapted to a preferred route of administration. Thus, a composition can be formulated to be administered via known routes including, for example, oral, parenteral (e.g., intradermal, transcutaneous, subcutaneous, intramuscular, intravenous, intraperitoneal, etc.), or topical (e.g., intranasal, intrapulmonary, intramammary, intravaginal, intrauterine, intradermal, transcutaneous, rectally, etc.). It is foreseen that a composition can be administered to a mucosal surface, such as by administration to, for example, the nasal or respiratory mucosa (e.g., by spray or aerosol). Also, a composition also can be administered via a sustained or delayed release.

A formulation may be conveniently presented in unit dosage form and may be prepared by methods well known in the art of pharmacy. Methods of preparing a composition with a pharmaceutically acceptable carrier include the step of bringing the isolated polypeptide into association with a carrier that constitutes one or more accessory ingredients. In general, a formulation may be prepared by uniformly and/or intimately bringing the active compound into association with a liquid carrier, a finely divided solid carrier, or both, and then, if necessary, shaping the product into the desired formulations.

The isolated polypeptide may be provided in any suitable form including but not limited to a solution, a suspension, an emulsion, a spray, an aerosol, or any form of mixture. The composition may be delivered in formulation with any pharmaceutically acceptable excipient, carrier, or vehicle. For example, the formulation may be delivered in a conventional topical dosage form such as, for example, a cream, an ointment, an aerosol formulation, a non-aerosol spray, a gel, a lotion, and the like. The formulation may further include one or more additives including such as, for example, an adjuvant, a skin penetration enhancer, a colorant, a fragrance, a flavoring, a moisturizer, a thickener, and the like.

Thus, in another aspect, this disclosure provides methods of providing treatment for tauopathy. As used herein, "treat," "treatment," or variations thereof refer to reducing, ameliorating, or resolving, to any extent, at least one symptom or clinical sign related to a tauopathic condition. As used herein, "ameliorate" refers to any reduction in the extent, severity, frequency, and/or likelihood of a symptom or clinical sign characteristic of a particular condition. The treatments described herein may be prophylactic and/or therapeutic. As used herein, "prophylactic" and variations thereof refer to a treatment that limits, to any extent, the development and/or appearance of a symptom or clinical sign of a tauopathic condition. As used herein, "therapeutic" and variations thereof refer to a treatment that ameliorates one or more existing symptoms or clinical signs associated with a tauopathic condition. As used herein, "sign" or "clinical sign" refers to an objective physical finding relating to a tauopathic condition capable of being found by one other than the patient. As used herein, "symptom" refers to any subjective evidence of tauopathic condition. The "subject" receiving treatment according to the methods described herein can include, for example, animals such as, but not limited to, humans, non-human primates, rodents, dogs, cats, horses, pigs, sheep, goats, or cows.

In some embodiments, the method generally includes administering to a subject having or at risk of having a tauopathic condition an amount of a pharmaceutical composition as described herein effective to inhibit to any of degree caspase-2 tau cleavage. In other embodiments, the method generally includes administering to a subject having or at risk of having a tauopathic condition an amount of a pharmaceutical composition as described herein effective to ameliorate at least one clinical sign or symptom characteristic of the tauopathic condition. In other embodiments, the method generally includes administering to a subject having or at risk of having a tauopathic condition an amount of a pharmaceutical composition as described herein effective to protect the subject against development of a tauopathic condition.

As used herein, "at risk" refers to a subject that may or may not actually possess the described risk. Thus, for example, a subject "at risk" for developing a tauopathic condition is a subject that possesses one or more indicia of increased risk of having, or developing, the specified condition compared to individuals who lack the one or more indicia, regardless of the whether the subject manifests any symptom or clinical sign of having or developing the condition. Exemplary indicia of tauopathic conditions can include, for example, mutations in certain genes (e.g., APP, PSEN1, PSEN2, CHMP2B, FUS, GRN, MAPT, TARDBP, VCP, and/or the APOE4 variant of APOE) and/or a family history of Alzheimer's disease or frontotemporal dementia. As used herein, "protect" refers to any delay in the onset of at least one symptom or clinical sign characteristic of a particular condition, or any reduction in the extent, severity, frequency, and/or likelihood of the onset of at least one symptom or clinical sign characteristic of a particular condition.

The amount of the isolated polypeptide administered can vary depending on various factors including, but not limited to, the specific isolated polypeptide, the weight, physical condition, and/or age of the subject, and/or the route of administration. Thus, the absolute weight of isolated polypeptide included in a given unit dosage form can vary widely, and depends upon factors such as the species, age, weight and physical condition of the subject, as well as the method of administration. Accordingly, it is not practical to set forth generally the amount that constitutes an amount of the isolated polypeptide effective for all possible applications. Those of ordinary skill in the art, however, can readily determine the appropriate amount with due consideration of such factors.

In some embodiments, the method can include administering sufficient [active agent] to provide a dose of, for example, from about 100 ng/kg to about 50 mg/kg to the subject, although in some embodiments the methods may be performed by administering the isolated polypeptide in a dose outside this range. In some of these embodiments, the method includes administering sufficient isolated polypeptide to provide a dose of from about 10 µg/kg to about 5 mg/kg to the subject, for example, a dose of from about 100 µg/kg to about 1 mg/kg.

Alternatively, the dose may be calculated using actual body weight obtained just prior to the beginning of a treatment course. For the dosages calculated in this way, body surface area ($m^2$) is calculated prior to the beginning of the treatment course using the Dubois method: $m^2=(wt\ kg^{0.425} \times height\ cm^{0.725}) \times 0.007184$.

In some embodiments, the method can include administering sufficient isolated polypeptide to provide a dose of, for example, from about 0.01 mg/$m^2$ to about 10 mg/$m^2$.

In some embodiments, the isolated polypeptide may be administered, for example, from a single dose to multiple doses per week, although in some embodiments the method can be performed by administering the isolated polypeptide at a frequency outside this range. In certain embodiments, the isolated polypeptide may be administered from about once per month to about five times per week.

In another aspect, we provide herein a novel assay for identifying additional inhibitors of caspase-2 tau cleavage. We have synthesized novel fluorescently N-terminal tagged polypeptides and used these novel tagged polypeptides to develop an assay that identifies inhibitors of caspase-2 tau cleavage. The assay involves combining a substrate polypeptide (e.g., SEQ ID NO:2 or SEQ ID NO:4) with caspase-2 and a test compound under conditions effective to allow the caspase-2 to cleave the substrate in the absence of the test compound. After a suitable incubation time, one can measure the mobility shift of the cleaved (product) and un-cleaved (substrate) peptides (e.g., using a Caliper LC3000 instrument). This assay is suitable for a high throughput screening campaign to identify novel compounds that inhibit caspase-2-dependent cleavage of the substrate.

Exemplary substrate/product polypeptide pairs used in the assay include FITC-AHX-GSVQIVYKPVDLSKVTS-COOH (SEQ ID NO:2) and FITC-AHX-GSVQIVYKPVD-COOH (SEQ ID NO:3), in which SEQ ID NO:3 is the caspase-2 cleavage product of substrate SEQ ID NO:2. In other embodiments, the substrate/product polypeptide pair can include FITC-AHX-GSVQIVYK(acetyl)PVDL-SKVTS-COOH (SEQ ID NO:4) and FITC-AHX-GSV-QIVYK(acetyl)PVD-COOH (SEQ ID NO:5), in which SEQ ID NO:5 is the caspase-2 cleavage product of substrate SEQ ID NO:4. The exemplary substrate/product polypeptide pairs are shown with FITC as a fluorescent label. However, the assay may be performed using any other suitable label or tag conventional for high throughput screening methods.

In some embodiments, the one or both polypeptides of the exemplary substrate/product polypeptide pairs identified immediately above may be a variant of SEQ ID NO:2, SEQ ID NO:3, SEQ ID NO:4 or SEQ ID NO:5 that includes one or more additional amino acids appended to either terminus of the indicated amino acid sequence so long as the substrate/product pair retains the stated caspase-2 cleavage substrate/product relationship. Molecular modeling algorithms make it routine for one to determine whether any particular variants of a substrate/product pair will adopt a conformation that will allow the variants to retain a caspase-2 cleavage substrate/product relationship. Thus, each member of a substrate/product pair can include an addition of, for example, 1, 2, 3, 4, 5, 6, 7, 8, 9, 10, 11, 12, 13, 14, 15, 16, 17, 18, 19, or 20 amino acid residues appended to either terminus of SEQ ID NO:2, SEQ ID NO:3, SEQ ID NO:4, or SEQ ID NO:5, with the proviso that the appended amino acid residues do not introduce additional caspase-2 cleavage sites.

In some embodiments, one or both polypeptides of a substrate/product pair may be a variant of SEQ ID NO:2, SEQ ID NO:3, SEQ ID NO:4 or SEQ ID NO:5 that includes one or more conservative substitutions so long as the substrate/product pair retains the stated caspase-2 cleavage substrate/product relationship. A conservative substitution for an amino acid in a substrate polypeptide or product polypeptide may be selected from other members of the class to which the amino acid belongs. For example, it is well-known in the art of protein biochemistry that an amino acid belonging to a grouping of amino acids having a particular size or characteristic (such as charge, hydrophobicity and hydrophilicity) can be substituted for another amino acid without altering the activity of a protein. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Conservative substitutions include, for example, Lys for Arg and vice versa to maintain a positive charge; Glu for Asp and vice versa to maintain a negative charge; Ser for Thr so that a free —OH is maintained; and Gln for Asn to maintain a free —NH$_2$.

In some embodiments, the one or both polypeptides of a substrate/product pair may be designed to provide additional sequences, such as, for example, the addition of coding sequences for added C-terminal or N-terminal amino acids that would facilitate purification by trapping on columns or use of antibodies. Such tags include, for example, histidine-rich tags that allow purification of polypeptides on nickel columns. Such gene modification techniques and suitable additional sequences are well known in the molecular biology arts.

In some embodiments, the one or both polypeptides of a substrate/product pair can include one or more post-expression modifications of the polypeptide such as for example, a glycosylation, an acetylation, a phosphorylation, and the like, or any combination of two or more such modifications. Here again, such modifications are permissible so long as the substrate/product pair retains the stated caspase-2 cleavage substrate/product relationship.

Additionally, in some embodiments, one or both of the polypeptides in a substrate/product pair can include any combination of two or more features of the various embodiments described above. Within a substrate/product pair, however, it is not necessary that the substrate polypeptide and the product polypeptide include identical modifications so long as the variant polypeptides retain their caspase-2 cleavage substrate/product relationship.

Since acetylation is a known mechanism of protein activity modulation, substrate SEQ ID NO:4 (or variants of SEQ ID NO:4 as described immediately above), for example, may be used in a similar mobility shift assay to detect deacetylation inhibitors. Alternatively, inhibitors of a transacetylase could be detected using the mobility shift of the appropriate paired sets of fluorescently tagged peptides and deacetylases and transacetylases.

In another aspect, this disclosure provides antibody preparations that include antibody that specifically binds to SEQ ID NO: 10 such as, for example, SEQ ID NO:12. As used herein, the term "antibody" without an article or adjectival modifier, generically refers to preparations that can include either a homogenous population of a single immunoglobulin molecule (e.g., a monoclonal antibody preparation) or a heterogeneous population of a plurality of immunoglobulin molecules (e.g., a polyclonal antibody preparation). As used herein, "specifically binds" and variations thereof refer to the character of exhibiting differential or a non-general (i.e., non-specific) affinity, to any degree, for a particular target such as, for example, SEQ ID NO:12. Thus, the term "specifically binds" does not imply or suggest that universally exclusive specific binding is required in order for, for example, an antibody to "specifically binds" a particular target.

Thus, the antibody preparation may be a polyclonal antibody preparation that specifically binds to SEQ ID NO:12 such as, for example, H1485, described in detail in the Examples section, below. Alternatively, the antibody preparation can include a monoclonal antibody that specifically binds to SEQ ID NO:12. The production of a monoclonal antibody that specifically binds to a particular polypeptide target is routine for those of skill in the art once the polypeptide target is identified using conventional methods.

In yet another aspect, this disclosure provides a method that generally includes contacting a biological sample from a subject that includes cerebral spinal fluid with an antibody preparation that includes antibody that specifically binds to SEQ ID NO:10 or specifically binds to SEQ ID NO:12, then detecting a ligand in the sample that specifically binds the antibody preparation. Detecting a ligand in the sample that specifically binds the antibody preparation can indicate that the subject from the sample is obtained has or is at risk of having a tauopathic condition. Thus, in some cases, the ligand to which the antibody preparation specifically binds can include the amino acids of SEQ ID NO:10 or the amino acids of SEQ ID NO:12 including, for example, a product of caspase-2 tau cleavage.

The method may be practiced using a sample obtained from a subject that exhibits one or more symptoms or clinical signs of a tauopathic conditions. In such circumstances, the method may confirm a diagnosis that the subject has a tauopathic condition. In other cases, the method may be practiced using a sample obtained from a subject that does not exhibit one or more symptoms or clinical signs of a tauopathic condition. In such circumstances, the method may be used to identify the subject from whom the sample is obtained as having or at risk of having a tauopathic condition.

In another aspect, this disclosure provides an aptamer preparation that includes one or more aptamers that specifically bind to SEQ ID NO:10 such as, for example, SEQ ID NO:12. As used herein, the term "aptamer" without an article or adjectival modifier, generically refers to a preparation that can include either a homogenous population of a single nucleotide sequence (e.g., a DNA or RNA aptamer preparation) or a homogenous population of a chemically-modified nucleotide sequence (e.g., a chemically-modified nucleotide aptamer preparation). In this context, too, "specifically binds" and variations thereof refer to the character of exhibiting differential or a non-general (i.e., non-specific) affinity, to any degree, for a particular target such as, for example, SEQ ID NO: 12. Thus, the term "specifically binds," in the context of an aptamer preparation, does not imply or suggest that universally exclusive specific binding is required in order for, for example, an aptamer to "specifically bind" a particular target.

Thus, the aptamer preparation may be a nucleotide sequence preparation that specifically binds to SEQ ID NO:10 or SEQ ID NO:12. Alternatively, the aptamer preparation can include a chemically-modified aptamer based on a developed nucleotide sequence that specifically binds to SEQ ID NO:10 or SEQ ID NO: 12. The production of a chemically-modified aptamer that specifically binds to a particular polypeptide target is routine for those of skill in the art once the parent nucleotide sequence is identified using conventional methods.

In yet another aspect, this disclosure provides a method that generally includes contacting a biological sample from a subject that includes cerebral spinal fluid with an aptamer preparation that includes aptamer that specifically binds to SEQ ID NO:10 or specifically binds to SEQ ID NO:12, then detecting a ligand in the sample that specifically binds the aptamer preparation. Detecting a ligand in the sample that specifically binds the aptamer preparation can indicate that the subject from the sample obtained, has, or is at risk of having a tauopathic condition. Thus, in some cases, the ligand to which the aptamer preparation specifically binds can include the amino acids of SEQ ID NO:10 or SEQ ID NO: 12 including, for example, a product of caspase-2 tau cleavage.

The method may be practiced using a sample obtained from a subject that exhibits one or more symptoms or clinical signs of a tauopathic conditions. In such circumstances, the method may confirm a diagnosis that the subject has a tauopathic condition. In other cases, the method may be practiced using a sample obtained from a subject that does not exhibit one or more symptoms or clinical signs of a tauopathic condition. In such circumstances, the method may be used to identify the subject from whom the sample is obtained as having, or at risk of having, a tauopathic condition.

This disclosure further provides a transgenic mouse model (rTg4510, described in the Examples section below) created to study the etiology of dementia in tauopathy. We found no relationship between neurofibrillary tangles and memory loss in rTg4510 mice, suggesting neurofibrillary tangles may represent an attempted neuroprotective sequestration of tau rather than a causative lesion underlying impairment. In addition, the data supported the possibility that the tau species responsible for inducing cognitive deficits is a functional protein that lies upstream of neurofibrillary tangle formation. The data indicated that memory function in rTg4510 mice improved when the production of soluble forms of tau was inhibited. Therefore, after eliminating tangles as a cause of memory loss in rTg4510 mice, we focused our studies on soluble forms of tau that precede the formation of neurofibrillary tangles.

Specifically, we sought to identify soluble forms of tau whose expression precedes the formation of tangles. Initially, we identified candidate tau* molecules (normalized densitometry) that inversely correlated with retention of spatial reference memory in a water maze, prior to neuron loss or tangle formation. We successfully used a similar strategy to identify the specific Aβ assembly responsible for the development of cognitive impairment in Tg2576 mice. We employed a 3-step procedure, modified from the one we used to examine Aβ oligomers, to separate tau peptides into distinct soluble extra/intracellular (S1), membrane-associated (S2) and insoluble pools.

Immunohistochemical (IHC) studies of rTg4510 show a consistent hierarchy for the expression of pathological tau epitopes, with CP-13 and MC-1 representing the earliest biochemical changes in tau. Following the IHC studies, we hypothesized that the biochemical alteration of tau that induced cognitive impairment would involve early pathological changes in these specific molecular states. However, we did not observe any substantial correlations (i.e., $r^2 > 0.5$) between biochemical expression and retention of spatial reference memory (Table 2). Further analysis of a panel of 12 antibodies failed to reveal close relationships between expression of specific 55 kDa (full-length) tau isoforms and memory function.

TABLE 2

Examples of epitopes that did not indicate a correlation between memory retention and 55 kDa tau expression

| Antibody | S1 (extra-/intra-cellular) | S2 (membrane-associated) |
| --- | --- | --- |
| MC-1 | $r^2 = 0.002$ | $r^2 = 0.006$ |
| CP-13 | $r^2 = 0.006$ | $r^2 = 0.001$ |
| PHF-1 | $r^2 = 0.190$ | $r^2 = 0.130$ |
| pThr$^{231}$ | $r^2 = 0.100$ | $r^2 = 0.050$ |
| AT180 | $r^2 = 0.002$ | $r^2 = 0.001$ |

We turned our attention to other possible biochemical changes that may underlie tau-induced memory dysfunction. We considered, for example, changes in phosphorylation, conformation, solubility, oligomerization, and cleavage that may represent changes in tau biochemistry that induce cognitive impairment. Our rTg4510 mice lacked tau fragments reported by others, including the tau fragment cleaved by multiple caspases at D421 (Gamblin et al., PNAS, 2003, 100 (17):10032-10037), the tau fragment cleaved by caspase-6 at D402 (Guo et al., Am J Path, 2004), the 17-kDa calpain-cleaved tau fragment that is involved in Aβ-dependent death of cultured neurons (Park & Ferreira, J Neurosci, 2005), and the thrombin-cleaved tau fragments found in tangles (Arai et al., J Biol Chem, 2005).

In the course of performing these correlation experiments, we consistently observed the presence of TCP35 in the brains of rTg4510 mice, particularly in the hippocampus and cortex. The levels of TCP35 were lower in cognitively intact age-matched rTg21221 mice expressing wild-type tau at levels equivalent to $tau_{P301L}$ in rTg4510, arguing against the possibility that TCP35 was an artifact caused by protein degradation while protein is being extracted from rTg4510 brain or during gel electrophoresis. When we examined the relative expression of TCP35 in relation to measures of behavior, we observed highly significant inverse relationships (FIG. 1).

Since memory deficits in rTg4510 mice develop in an age-dependent fashion, we also examined the expression of TCP35 at different ages and found that the expression of TCP35 parallels the development of impaired memory (FIG. 2). Taken together, the data indicate that TCP35 correlates with cognitive impairment prior to the onset of neurodegeneration in rTg4510 mice.

Figure 3:
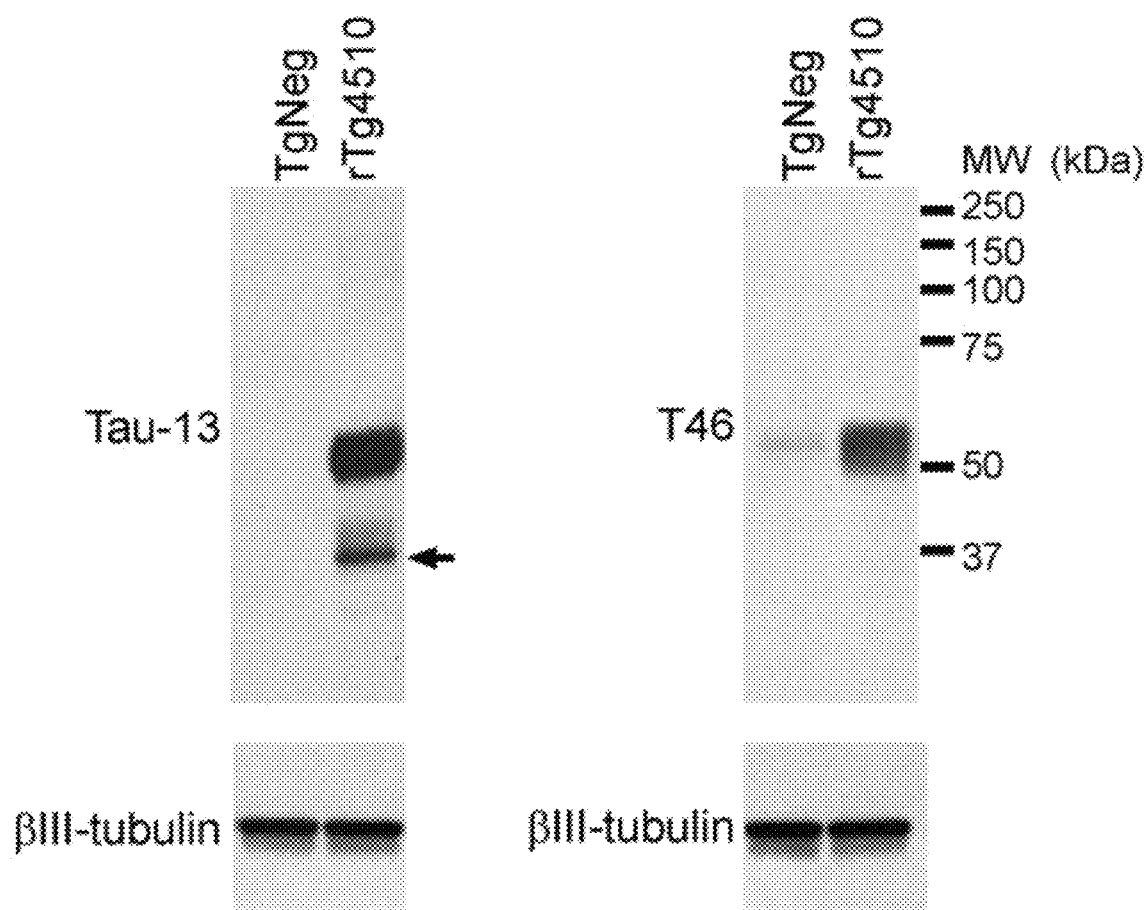
FIG. 3. TCP35 is an N-terminal fragment of tau. Representative immunoblots of tau proteins in forebrain homogenates of TgNeg and rTg4510 mice. (A) TCP35 can be detected by Tau-13 mAb, which specifically recognizes amino acid residues 2-18 in human tau, (B) but not by T46 mAb, which recognizes an epitope near the last 38 amino acid residues (404-441 aa) on the C-terminus of tau. βIII-tubulin was probed to ensure loading consistency.
Figure 4:
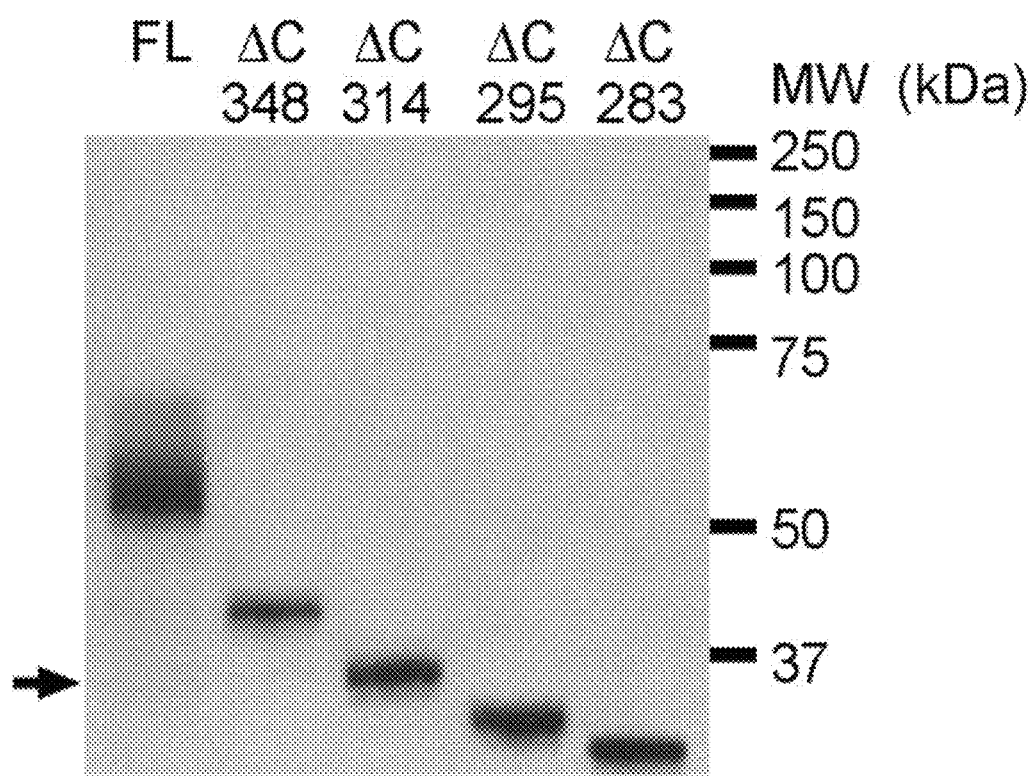
FIG. 4. Identification of caspase-2 cleavage site in tau. Full-length (FL) tau and truncation mutant proteins that are missing the C-terminus after four aspartate residues mimicking tau cleaved at D283, D295, D314 and D348 were synthesized from the corresponding cDNAs using the TNT T7 Quick Coupled Transcription/Translation System. Immunoblotting using Tau-13 mAb showed that tau truncation mutant ΔC314 is closest to 35 kDa in molecular weight.

Next, we characterized TCP35. On the basis of the immunospecificity of TCP35 on western blots, we deduced that TCP35 is an N-terminal fragment of tau (FIG. 3). Caspases typically cleave after aspartate residues, providing the opportunity to examine the molecular weights of a series of recombinant proteins mimicking tau, cleaved at the four aspartate residues located in the region in tau that, when cleaved, would generate a fragment approximating 35 kDa. One truncation mutant, tauΔC314, most closely approximated TCP35 in molecular weight (FIG. 4).

Figure 5:
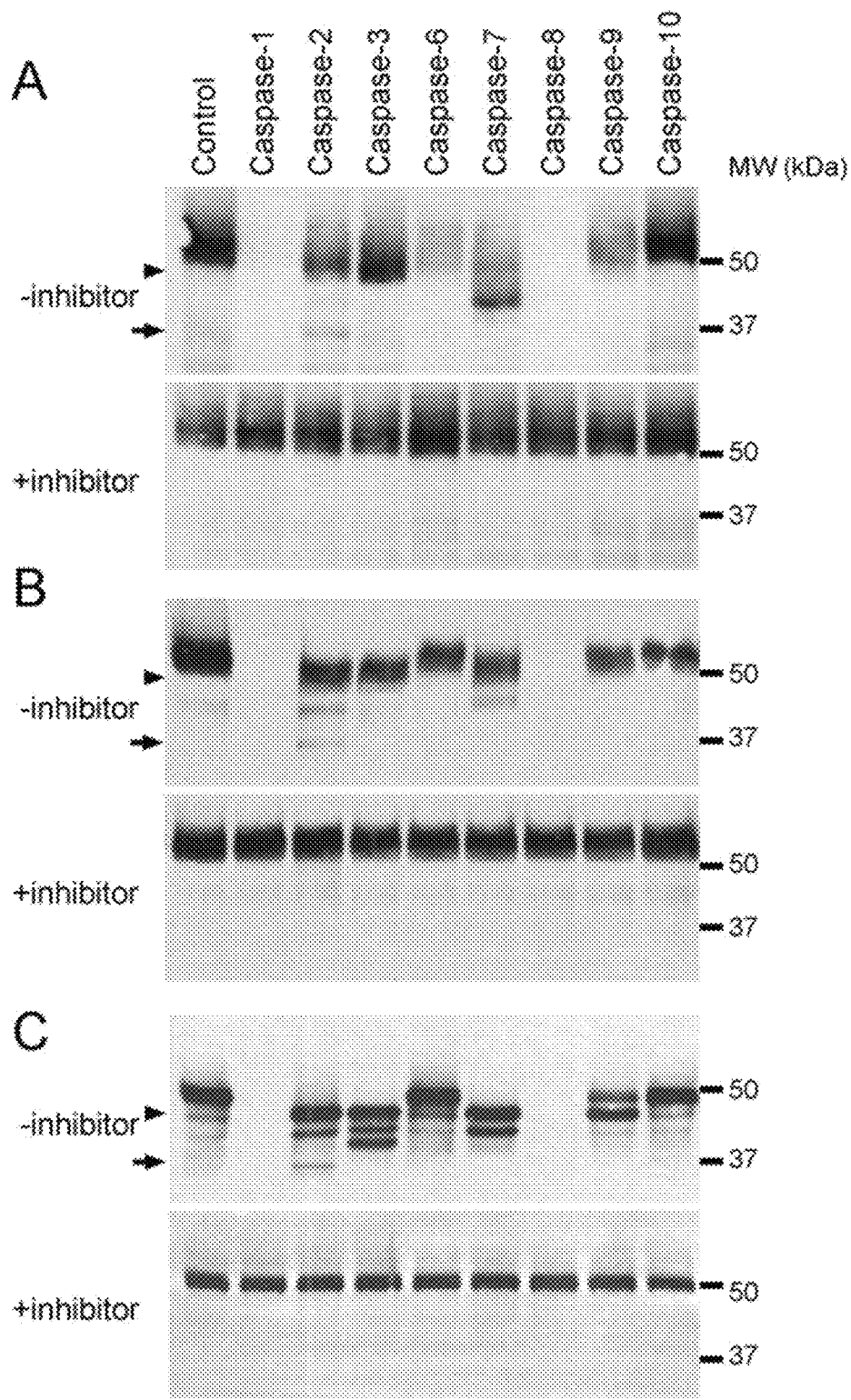
FIG. 5. Caspase-2 cleaves tau in vitro, producing a 35 kDa fragment. Recombinant caspases-1, -2, -3, -6, -7, -8, -9, or -10 were incubated at 37° C. for 2 hours with tau proteins derived from three different sources. Immunoblots using Tau-13 mAb showed a 35 kDa fragment generated by co-incubating caspase-2 with full-length tau proteins purified from (A) brain lysates of Tg4510 mice expressing human $tau_{P301L}$, (B) brain lysates of rTg21221 mice expressing human wild-type tau ($tau_{WT}$) (Hoover et al., Neuron, 2010), or (C) synthetic human $tau_{WT}$. 50 μM z-VAD-fmk (benzyloxycarbonyl-Val-Ala-Asp-fluoromethylketone; Sigma-Aldrich; St. Louis, Mo.) (+inhibitor), a general caspase inhibitor, blocked all cleavage. Caspases-1 and -8 may cleave tau proteins near the N-terminus and remove Tau-13 mAb epitopes, preventing detection of proteolytic products. Arrows denote the 35 kDa fragment, and arrowheads denote the tau fragment truncated at D421.

We next assayed the ability of each of the eight different caspases expressed in the brain to cleave tau purified from brain extracts from tau-expressing transgenic mice or synthesized using recombinant methods. Only one of the caspases, caspase-2, generated a 35 kDa tau fragment (FIG. 5), presumably recognizing the non-canonical cleavage sequence $KPVD_{314}$ (SEQ ID NO:24), albeit cleaving with significantly less efficiency than at D421. In most cells caspase-2 localizes to the nucleus, but in neurons caspase-2 is cytosolic, where it would have access to tau, a necessary requirement for implicating this protease.

Figure 6:
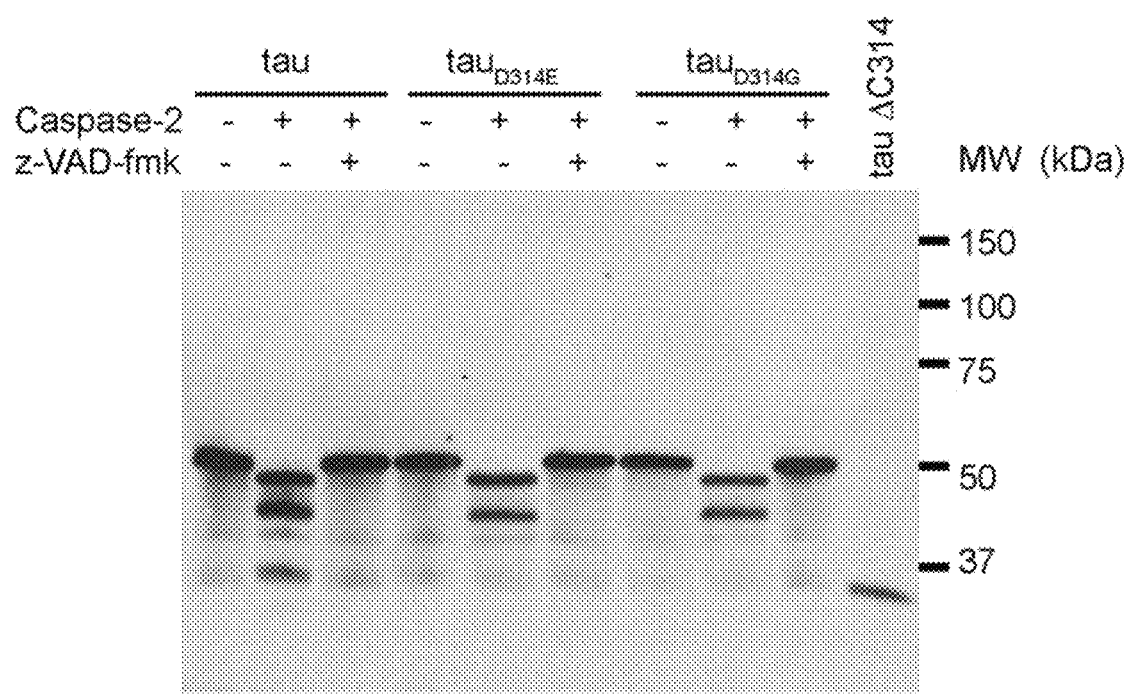
FIG. 6. A 35 kDa fragment is produced by caspase-2-mediated cleavage at D314 in vitro. Incubation of recombinant caspase-2 with wild-type tau or tau mutants, $tau_{D314E}$ and $tau_{D314G}$, that resist caspase cleavage, synthesized from the corresponding cDNAs using the TNT T7 Quick Coupled Transcription/Translation System, generated a 35 kDa fragment only in the wild-type tau reaction that comigrates with tau truncation mutant ΔC314. The arrow denotes the 35 kDa fragment. The arrowhead denotes the tau D421 cleavage product.

We then prepared tau mutants D314E and D314G that resisted caspase-2 cleavage (FIG. 6), further supporting our hypothesis that TCP35 is generated when tau is cleaved by caspase-2 at D314.

Figure 7:
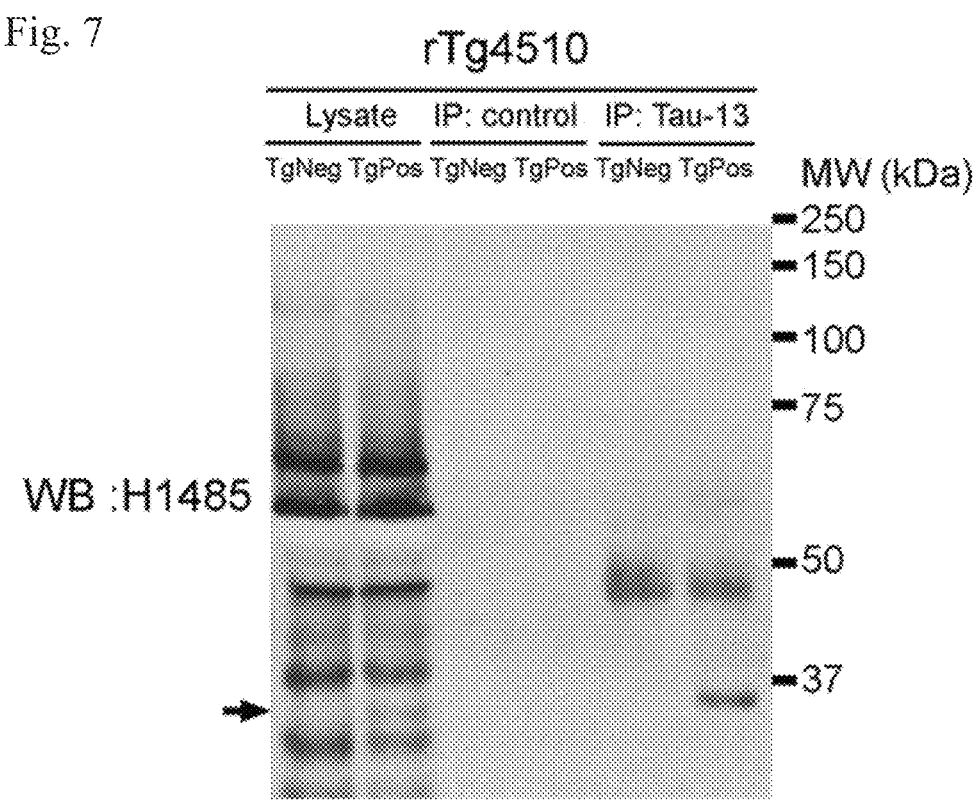
FIG. 7. Cleavage-specific polyclonal antibodies H1485 recognize a 35 kDa band in rTg4510 brain. H1485 antibodies were generated against the neo-epitope of caspase-2 cleaved tau at D314. rTg4510 brain lysate was immunoprecipitated with Tau-13 mAb. The immunoprecipitates were detected on immunoblots with H1485 antibodies, revealing a 35 kDa band in rTg4510 brain (arrow).

Next, we generated H1485 polyclonal antibodies specifically recognizing the C-terminal neo-epitope of tauΔC314 to probe brain extracts from impaired rTg4510 mice. In rTg4510 (Tau-positive) but not TgNeg mice, we found a 35 kDa H1485-immunoreactive band that co-migrates with TCP35 in brain proteins that were immunoprecipitated with Tau-13 mAbs (FIG. 7). The data provide further support for our hypothesis that caspase-2 cleavage at tau D314 generates TCP35.

Figure 13:
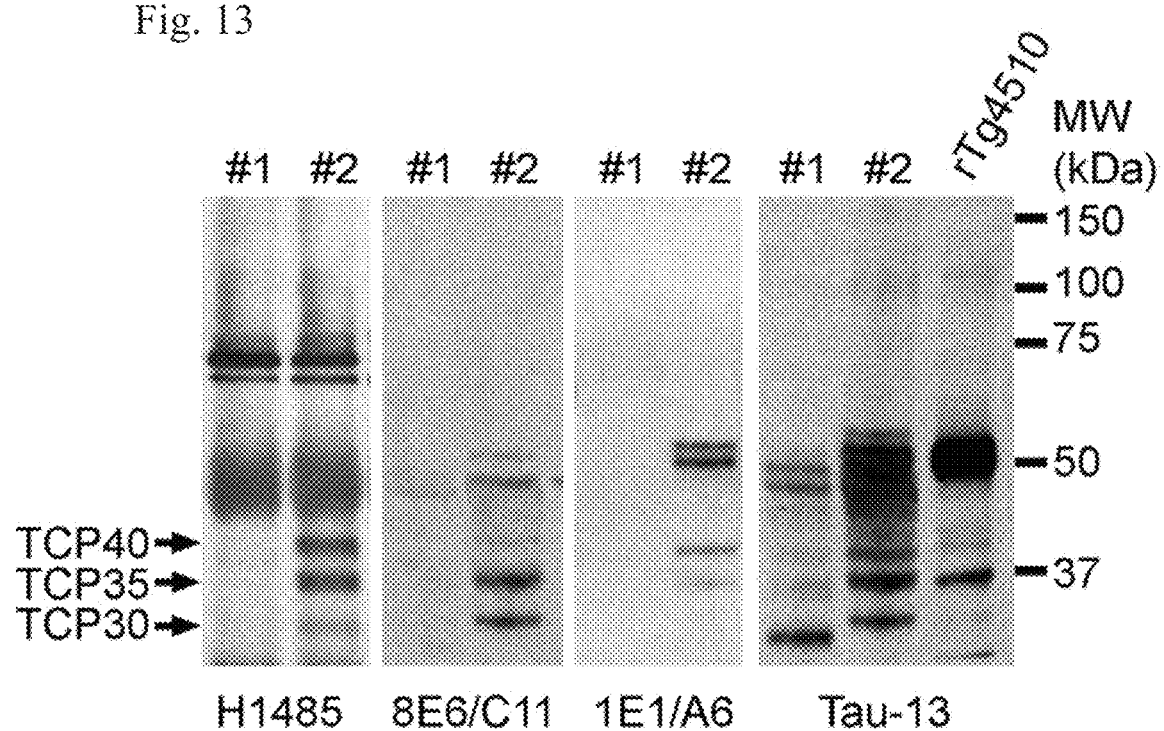
FIG. 13. Profile of tau cleavage product in human brain lysates. Human brain lysates were probed with cleavage site-specific antibody H1485, 3-repeat isoform antibody 8E6/C11, 4-repeat isoform antibody 1E1/A6 and total tau antibody Tau-13. Three tau fragments TCP40, TCP35 and TCP30 were recognized by H1485 antibody.

In some embodiments, TCP35 can include a polypeptide having the amino acid sequence depicted in SEQ ID NO:16. In other embodiments, TCP35 can include a polypeptide having the amino acid sequence depicted in SEQ ID NO:17. The H1485 polyclonal antibody also recognizes TCP40 cleavage products (SEQ ID NO:14 and SEQ ID NO:15) and a TCP30 tau cleavage product (SEQ ID NO:18) (FIG. 13).

Figure 14:
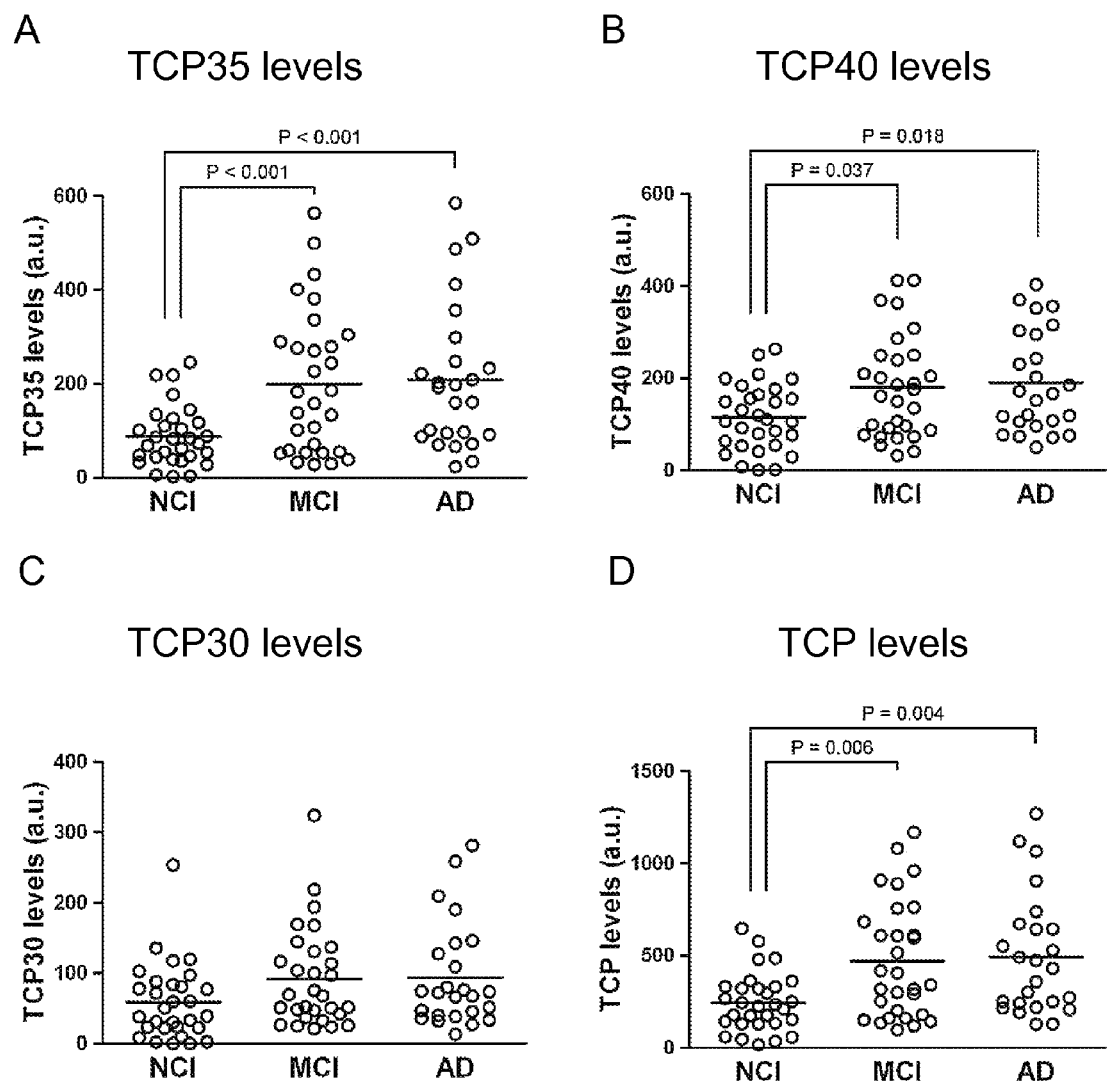
FIG. 14. Tau cleavage product levels increase in patients with mild cognitive impairment and Alzheimer's disease. The protein levels of (A) TCP35, (B) TCP40 and (C) TCP30 were quantified, respectively. (D) The total protein levels of TCP35, TCP40 and TCP30 (TCP) were also quantified.

Tau cleavage product levels increase in patients with mild cognitive impairment and Alzheimer's disease. The protein levels of TCP35, TCP40, and TCP30 were quantified, respectively (FIG. 14). The total protein levels of TCP35, TCP40 and TCP30 (TCP) were also quantified.

Figure 15:
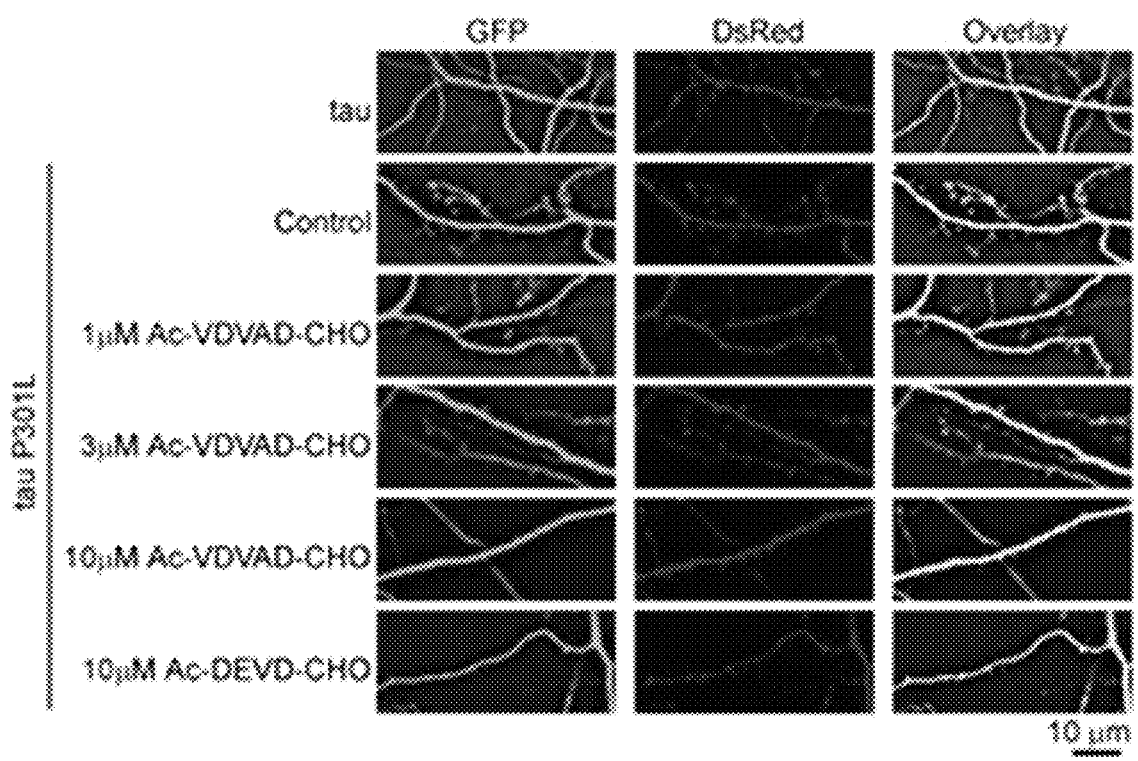
FIG. 15. Images of rat hippocampal neurons coexpressing Dsred and GFP-tagged wild-type tau or tau P301L mutant. Neurons were treated with caspase-2 inhibitor Ac-VDVAD-CHO or caspase-3 inhibitor Ac-DEVD-CHO for 1 day.
Figure 16:
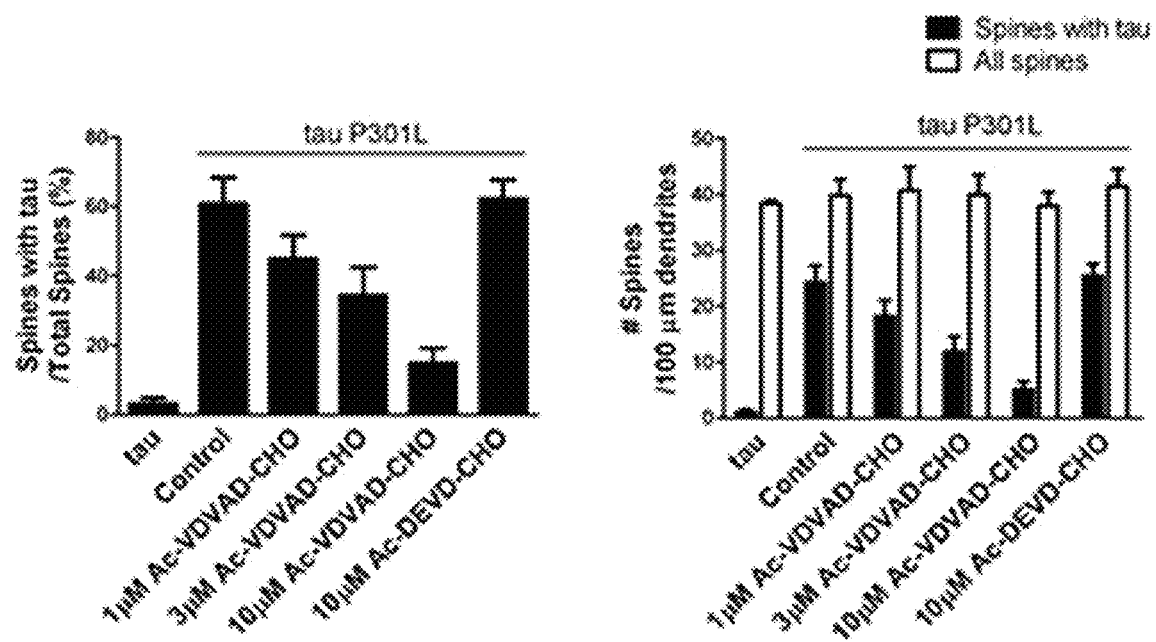
FIG. 16. Quantification of total spines and GFP-tau-containing spines in neurons coexpressing DsRed and GFP-tau.
Figure 17:
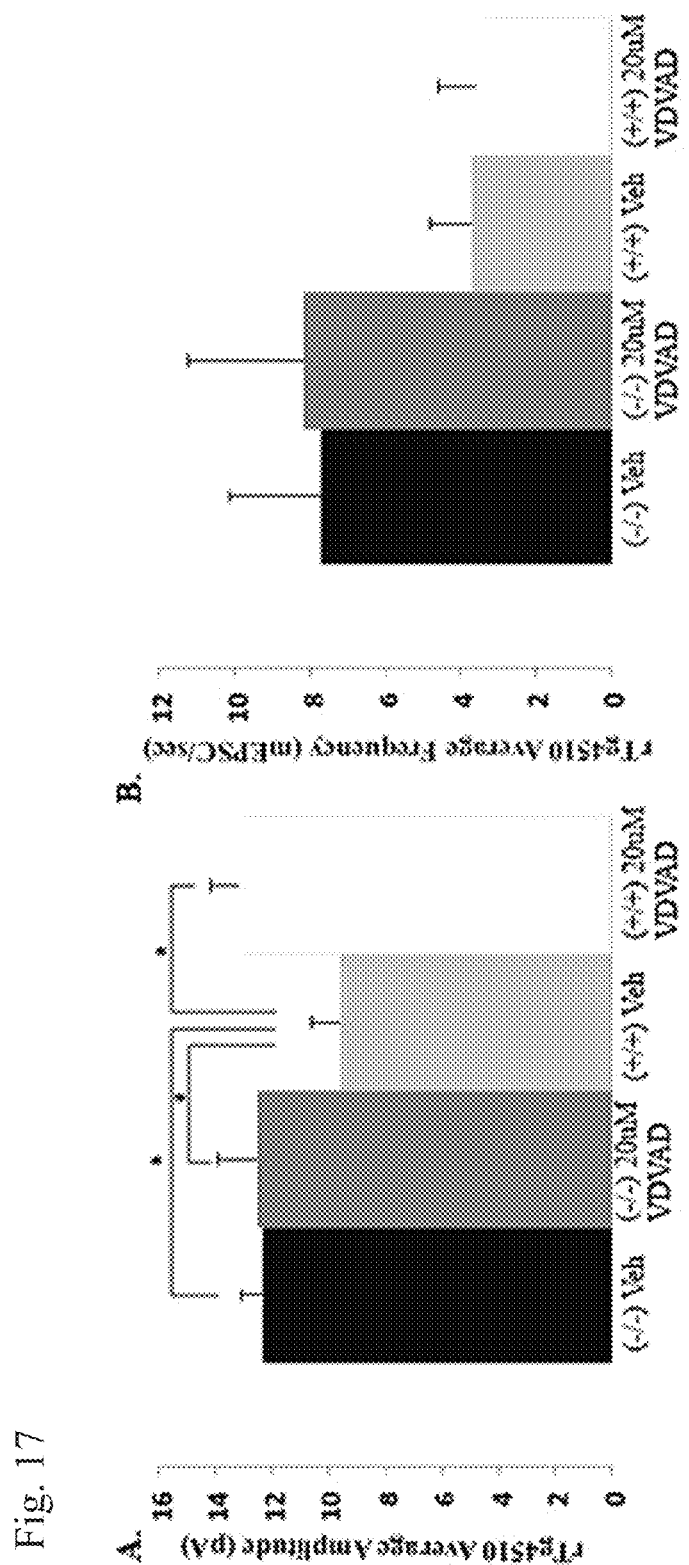
FIG. 17. Excitatory Synaptic Transmission in rTg4510 neurons treated with caspase-2 inhibitor. (A) Mean mEPSC amplitudes of rTg4510 neurons (−/− and +/+) treated with 20 μM caspase-2 inhibitor (Ac-VDVAD-CHO; SEQ ID NO:35) for two hours. Caspase-2 inhibitor significantly increased the mean amplitude of AMPA (α-amino-3-hydroxy-5-methyl-4-isoxazolepropionic acid) mEPSCs in rTg4510 (+/+) neurons compared to vehicle (Veh) control. Caspase-2 inhibitor had no effect on rTg4510 (−/−) neurons. (B) Mean mEPSC frequency of rTg4510 neurons (−/− and +/+) treated with 20 μM caspase-2 inhibitor for two hours. Caspase-2 inhibitor had no effect on rTg4510 neurons (−/− or +/+) frequencies.
Figure 20:
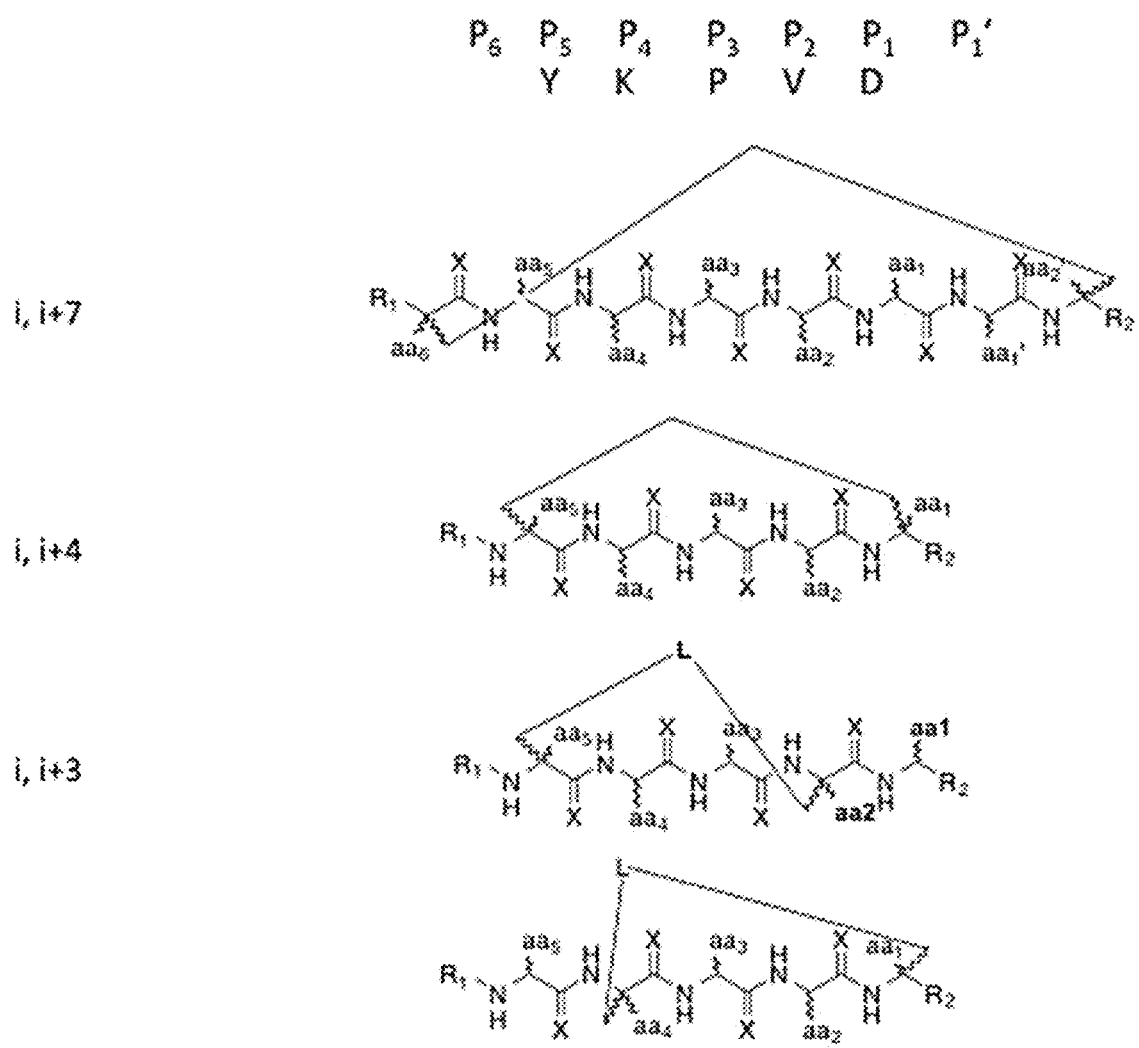
FIG. 20. Generalized design of macrocyclic/stapled peptides based on i, i+3, i+4, and i+7 strategies, where L=Linker (e.g., linkers described in International Publication No. WO 2013/123266 A1), and X is O or S.

Images of rat hippocampal neurons coexpressing Dsred and GFP-tagged wild-type tau or tau P301L mutant are shown in FIG. 15. Neurons were treated with caspase-2 inhibitor Ac-VDVAD-CHO (SEQ ID NO:36) or caspase-3 inhibitor Ac-DEVD-CHO (SEQ ID NO:37) for 1 day. FIG. 16 shows the quantification of total spines and GFP-tau-containing spines in neurons coexpressing DsRed and GFP-tau. As the concentration of caspase-2 inhibitor increases, the number of spines with tau decreases.

The observations that (1) TCP35 appears at 4.5 months, when cognition declines, (2) TCP35 exhibits a statistically significant correlation with memory impairment, (3) TCP35 co-migrates with both tauΔC314 and a tau fragment generated following incubation with caspase-2, and (4) tauΔC314 is present in rTg4510 but not TgNeg brain extracts suggest that TCP35 is tau* and that caspase-2 cleaves tau at D314 to generate TCP35. These data, however, are correlative rather than causative. Thus, we next determined whether TCP35 causes neuronal dysfunction. We began by assaying its effects on dendritic spines, which are loci of synaptic plasticity underlying learning and memory.

Healthy neurons maintain a spatial gradient of tau, whose concentration is greater in axons than in somatodendritic compartments. In neurological disorders such as Alzheimer's disease, the gradient becomes inverted. One consequence of this inversion is aberrant accumulation of tau within intact dendritic spines, where it can disrupt synaptic function by impairing glutamate receptor trafficking and/or synaptic anchoring. We tracked chimeric tau molecules tagged at the N-terminus with GFP and found that the P301L mutation and pseudo-hyperphosphorylation of tau both enhance its mislocalization to spines, with hyperphosphorylation appearing downstream of the mutation since pseudo-hyperphosphorylation is sufficient to misdirect wild-type tau and blocking phosphorylation prevents the mislocalization of $tau_{P301L}$. The abnormal presence of tau in spines corresponded to a reduction in the clustering of both AMPA and NMDA receptors in spines, resulting in smaller amplitudes and frequencies of miniature excitatory post-synaptic currents (mEPSCs).

Figure 8:
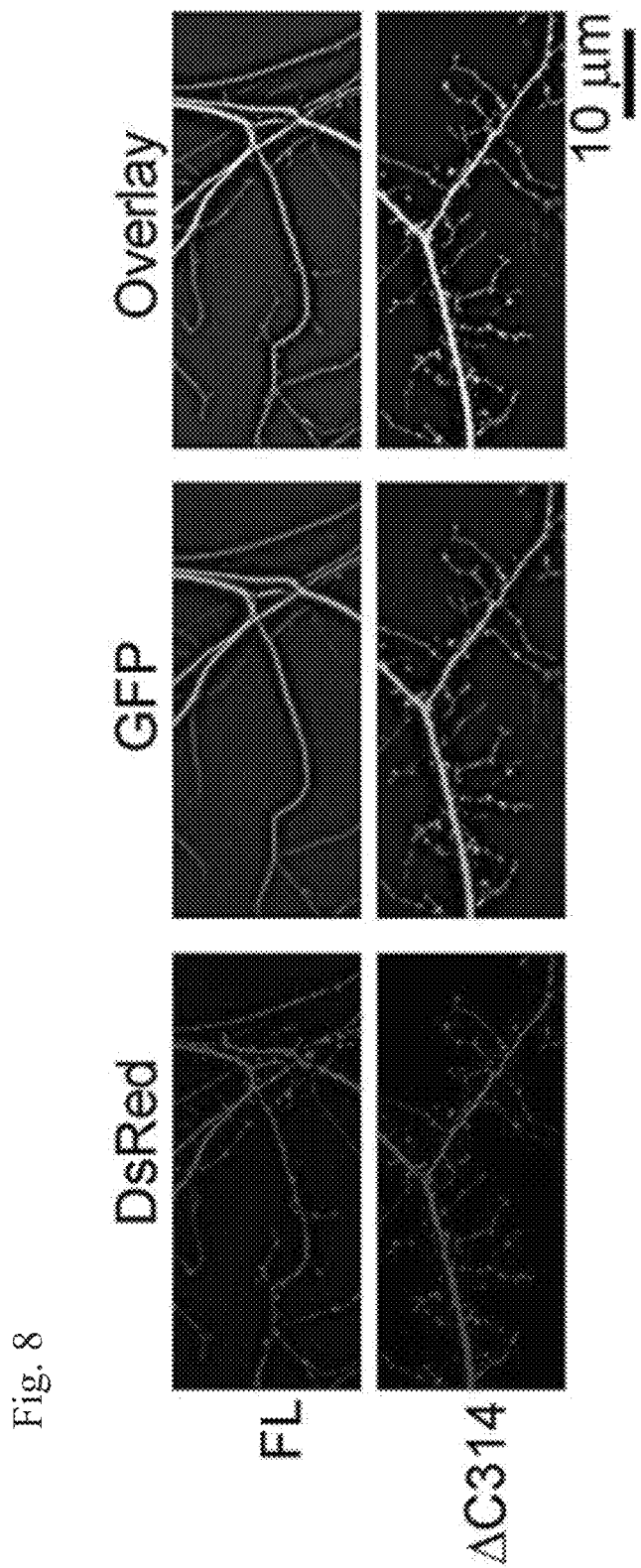
FIG. 8. TauΔC314 mislocalizes to dendritic spines. Images of rat hippocampal neurons co-expressing DsRed, which permeates all dendritic spines and shafts permitting their visualization, and GFP-tagged full-length tau (FL) or the tauΔC314 mutant, show aberrant targeting of tauΔC314 to dendritic spines.
Figure 9:
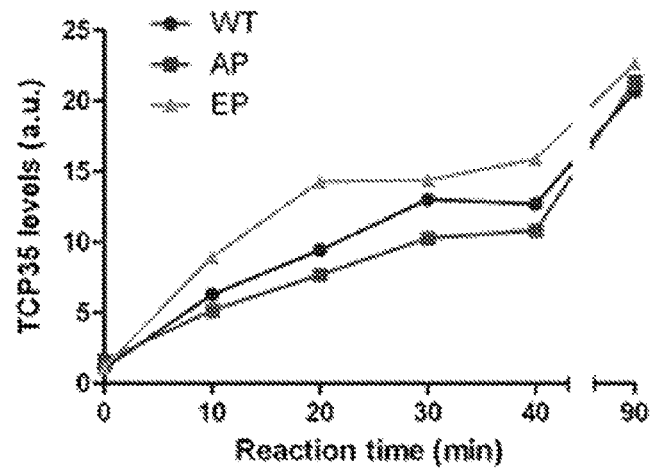
FIG. 9. Effects of proline-directed phosphorylation on in vitro TCP35 generation. Wild-type (WT), phosphorylation-deficient (AP) and pseudophosphorylated (EP) tau proteins are synthesized from the corresponding cDNAs in vitro by using the TNT T7 Quick Coupled Transcription/Translation System. Recombinant caspase-2 was incubated with tau proteins to generate TCP35 and the reactions were stopped at the indicated time points. TCP35 was immunoblotted with Tau-13 mAb.
Figure 10:
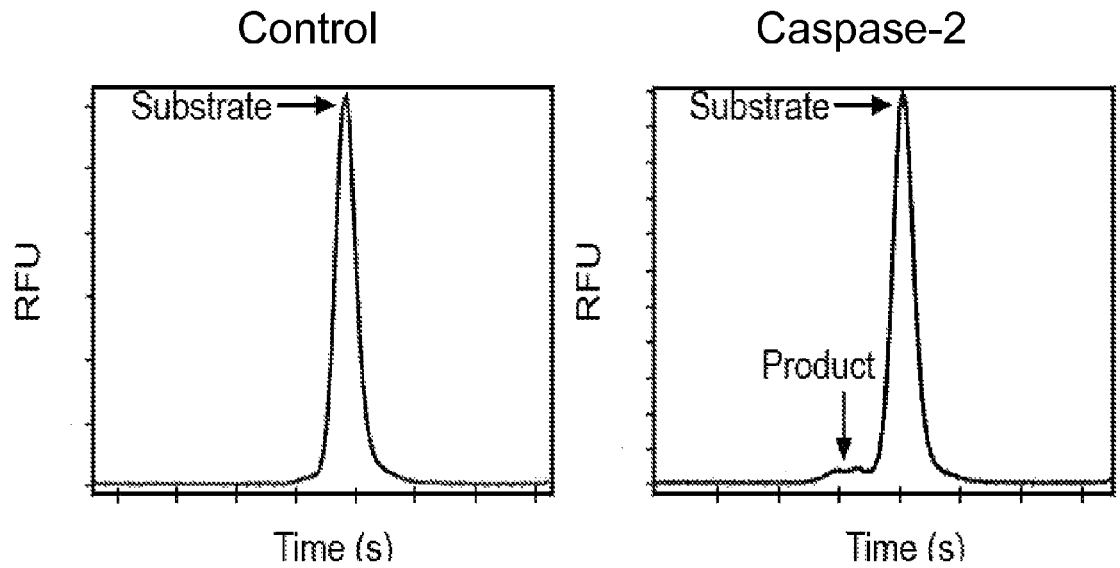
FIG. 10. Caspase-2-mediated cleavage of Asp314 peptide substrate. Synthetic peptide substrate FITC-AHX-GSV-QIVYKPVDLSKVTS-COOH was designed based on amino acids 304-320 of tau protein that encompasses Asp314 cleavage site. The peptide substrate was cleaved by coincubating with recombinant caspase-2 and was separated from cleavage product by using LabChip drug discovery system. The fluorescence emitted by FITC group was monitored to measure peptide quantity.
Figure 11:
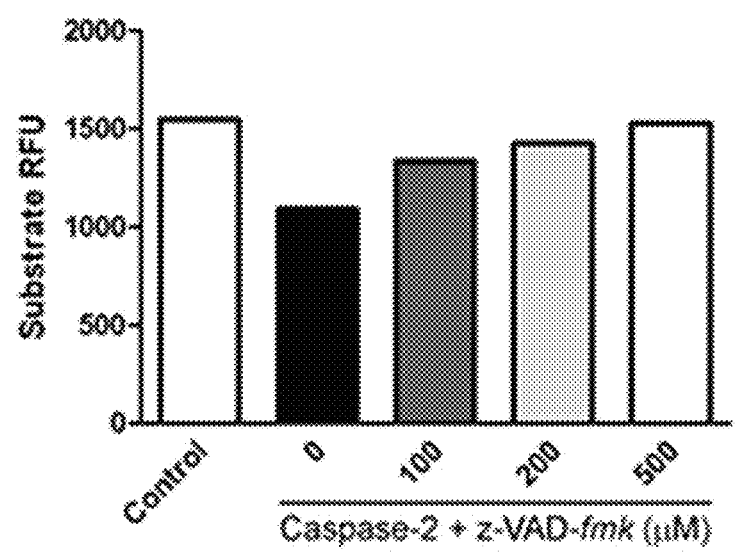
FIG. 11. Caspase inhibitor blocks caspase-2-mediated cleavage of Asp314 peptide substrate. Synthetic peptide substrate was coincubated with recombinant caspase-2 in the presence of general caspase inhibitor z-VAD-fmk. The fluorescence of the substrate peptide was measured by using LabChip drug discovery system.

In these experiments, we could not assess the role of TCP35 in mediating tau mislocalization and subsequent synaptic impairment because the GFP-tagged tau variants did not distinguish between full-length and truncated tau. In our initial experiments to determine whether TCP35 has the potential to disrupt neuronal function, we expressed GFP-tagged tauΔC314 in rat primary neuronal cultures and found that, like $tau_{P301L}$ and pseudo-hyperphosphorylated tau, tauΔC314 also mislocalizes to dendritic spines (FIG. 8). We noted that wild-type tau did not mislocalize, although caspase-2 cleaves wild-type recombinant tau in vitro. Caspase-2 cleavage of wild-type in neurons may involve phosphorylation.

The family of mammalian caspases shows close homology to the C. elegans apoptotic protein CED-3, and caspase-2 is the most conserved member of this family. Mammalian caspases possess many different functions beyond mediating apoptosis. Indeed, their non-death activities may be evolutionarily older than their lethal functions. For example, in addition to its involvement in specific types of apoptosis, caspase-2 also functions in DNA repair, cell cycle regulation and tumor suppression. These cellular pathways may be involved in Alzheimer's and other neurodegenerative diseases.

To determine whether cleavage of tau by caspase-2 mediates tau mislocalization in cultured neurons, one can examine tau trafficking in neurons derived from caspase-2 null mice, which are commercially available from vendors such as, for example, can be obtained from The Jackson Laboratory (Bar Harbor, Me.). One can determine whether the absence of caspase-2 prevents the mislocalization of pseudo-hyperphosphorylated tau and $tau_{P301L}$. If so, caspase-2 may mediate tau mislocalization.

TauΔC314 mislocalizes to spines (FIG. 8). Moreover, tau phosphorylation at 14 proline-directed serine and threonine sites (SP/TP) potentiates tau mislocalization. Conversely, preventing phosphorylation at the SP/TP sites blocks $tau_{P301L}$ mislocalization. To determine the order of the cleavage and phosphorylation events, one can prepare a series of GFP-tagged tauΔC314 and $tau_{D314E}$ variants in which one can change the SP/TP residues to, for example, either (1) non-polar alanine residues to prevent phosphorylation, termed AP for alanine-proline, or (2) negatively charged glutamate residues to mimic phosphorylation, termed EP for glutamate-proline. Particularly informative data can be obtained from experiments involving tauΔC314 in the AP tau variant and $tau_{D314E}$ in the EP tau variant. For example, when cleavage followed by SP/TP phosphorylation results in tau mislocalization, then tauΔC314 in the AP tau variant may not mislocalize to spines. When cleavage is downstream of SP/TP phosphorylation, then mislocalization of tauΔC314 may occur in both the AP and the EP tau variants. A practical implication of cleavage occurring downstream of hyperphosphorylation may be the possibility of targeting caspase-2 rather than tau kinases. Such a strategy may produce a lower chance of undesirable—even dangerous—side effects, given how few deficits occur in caspase-2 null mice.

Using the neurons generated to address the previous two questions, one can examine the pattern of glutamate receptors (NR1, GluR1, GluR2/3) by immunolocalization and measure the amplitude and frequency of mEPSCs by patch clamping. These data can establish the extent to which the cleavage of tau by caspase-2 in neurons affects synaptic function.

The presence of tau in dendritic spines can mediate brain dysfunction in Aβ and tau mouse models. However, contrasting mechanisms of action have been proposed: a) in one model it is the ability of tau in spines to stabilize NMDA receptor activity that mediates Aβ-induced memory dysfunction (Ittner et al., *Cell*, 2010); b) in another model it is the ability of tau in spines to decrease NMDA and AMPA receptor activation that mediates tau-induced memory dysfunction (Hoover et al., *Neuron*, 2010). In neither model, however, has the specific form of tau that mediates memory loss been identified in vivo. Thus, our identification of TCP35 represents an advance regardless of the mechanism of tau-induced brain dysfunction.

One can assess the role of TCP35 by genetically ablating caspase-2 in rTg4510 mice, which should substantially limit—perhaps even eliminate—the presence of TCP35. TCP35 levels can be monitored using, for example, Tau-13 mAb and H1485 neo-epitope antibodies. rTg4510 ("r" for regulatable) may be generated by mating activator (129S6-TgtTA) and responder (FVB-Tg4510) mice. Caspase-2 null mice are in a B6 background strain. To obtain the desired mice, one can breed hemizygous caspase-2 activator and responder mice in this exemplary cross:

129S6B6F1-TgtTA$^{caspase-2\Phi/+}$×FVBB6F1-Tg4510$^{caspase-2\Phi/+}$.

Only 1:16 offspring will be rTg4510$^{caspase-2\ \Phi/\Phi}$ or rTg4510$^{caspase-2+/+}$ mice.

Since caspase-2 null mice have intact memory function, one can use caspase-2 null mice to determine whether caspase-2 is required for rTg4510 mice to develop memory deficits by comparing memory function in rTg4510 caspase-2 null (rTg4510$^{caspase-2\ \Phi/\Phi}$) mice and rTg4510$^{caspase-2+/+}$ littermates.

One also can perform longitudinal behavioral testing in these crosses to assess behavior both before and after the onset of deficits, in order to test the null hypothesis that there is no significant age by caspase-2 interaction. One can test memory using a water maze. However, because the water maze can be difficult to interpret in longitudinal tests, one can supplement the water maze with, for example, one or more of three operant tests: 1) fixed consecutive number test of cortical function; 2) delayed non-matching to sample test of hippocampal function; and 3) active avoidance test of hippocampal function.

Figure 12:
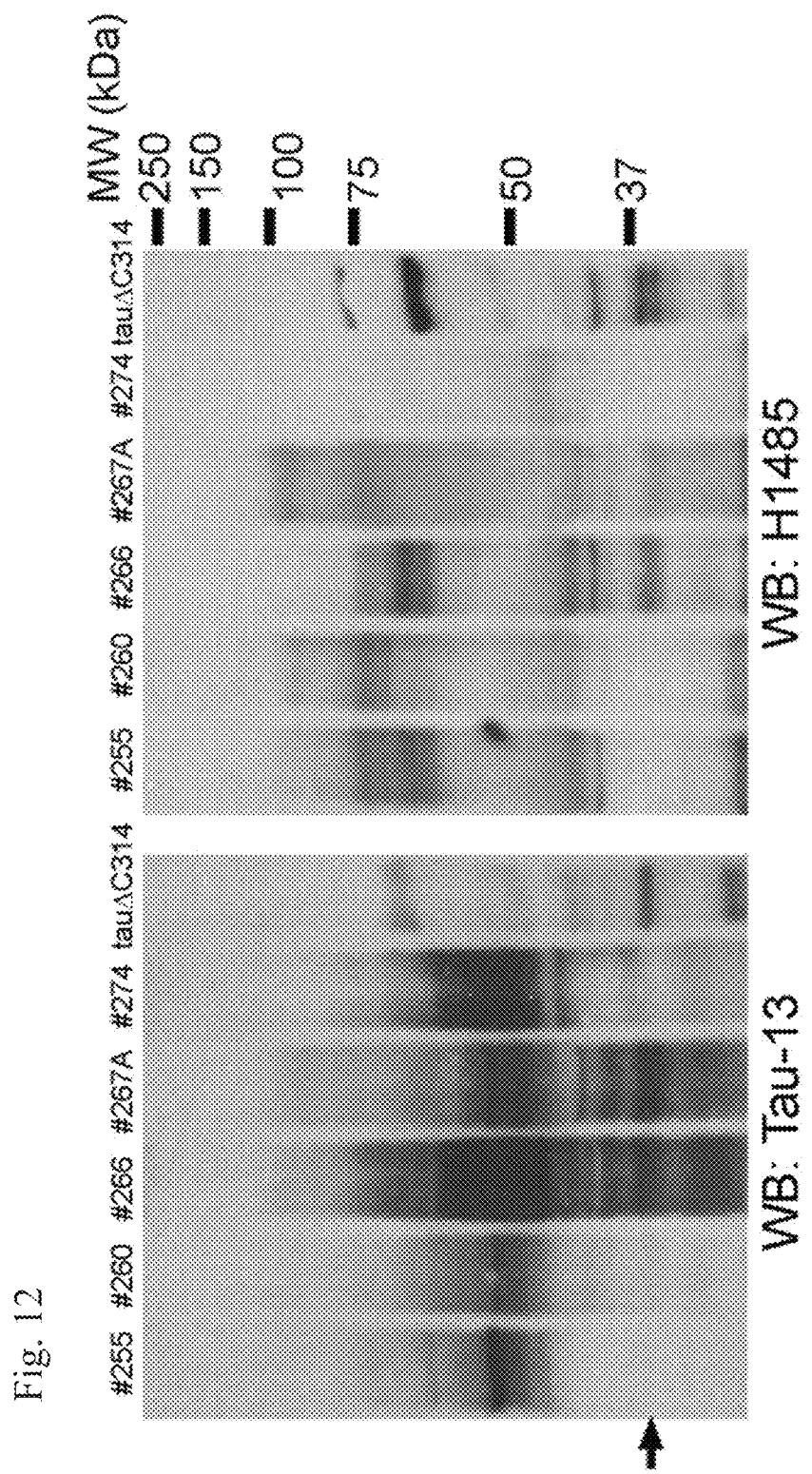
FIG. 12. TCP35 is present in human cerebrospinal fluid. Tau proteins were immunoprecipitated from human cerebrospinal fluid with Tau-13 mAb. The immunoprecipitates were detected on immunoblots with Tau-13 and H1485 antibodies, respectively, revealing TCP35 bands (arrow) in samples #266 and #267A. Tau truncation mutant ΔC314 was probed to show the comigration with TCP35.

Finally, one can examine human frontal cortex specimens for the presence of TCP35. Suitable specimens include specimens obtained from, for example, the Memory and Aging Project (MAP) from elderly community-dwelling volunteers with no cognitive impairment, mild cognitive impairment, Alzheimer's disease, or frontotemporal dementia. An antibody such as, for example, H1485 neo-epitope antibodies to tauΔC314 may be used to measure TCP35 in brain tissue from samples obtained from subjects (e.g., MAP specimens). FIG. 12 shows the identification of TCP35 in human cerebrospinal fluid obtained from subjects diagnosed with tauopathy.

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

The rTg4510 Mouse Model

To study the etiology of dementia in tauopathy, we created a transgenic mouse model expressing the P301L mutation in human tau (tau$_{P301L}$) linked to a dominantly inherited tauopathy. In an age dependent manner these mice develop: i) neurofibrillary pathology; ii) forebrain specific neurodegeneration; and memory impairment and/or dementia. Pathological biochemical changes in tau are detected from 2.5 months of age. The onset of memory deficits is first observed at 2.5 months and is significant at 4 months. Mature neurofibrillary tangles appear at 4 months. Significant neuronal loss is estimated by stereology to occur at 5.5 months and is most striking in the hippocampus CA1 subfield. For a comprehensive description see Ramsden et al., *J. Neurosci.*, 2005, 25:10637-10647.

One feature of rTg4510, compared to many other tau transgenic mice, is the preservation of motor function, achieved by engineering the transgene to avoid expression in the brainstem, which permits the clean interpretation of cognitive tests uncomplicated by motor or sensory abnormalities. Another feature of rTg4510 is that the first neurological deficits appear at a few months of age, compared with one or two years of age in many other models. The early onset of tauopathy in rTg4510, achieved by overexpressing the human tau transgene, allows one to perform our studies relatively quickly.

Example 1

Animals

Briefly, rTg(tauP301L)4510 and rTg(tauWT)21221 mice were generated using a system of responder and activator transgenes to achieve regulatable expression (Hoover et al., *Neuron*, 2010). Mice expressing the activator transgenes were derived following a generous gift from Dr. E. Kandel (Columbia University, New York, N.Y.) (Mayford et al., *Science*, 1996) and successively backcrossed a minimum of five times onto a 12956 background strain. Responder mice were maintained in the FVB/N strain. Mice were screened by PCR using the primer pairs 5'-GATTAACAGCGCATTAGAGCTG-3' (SEQ ID NO:6) and 5'-GCATATGATCAATTCAAGGC-CGATAAG-3' (SEQ ID NO:7) for activator transgenes and 5'-TGAACCAGGATGGCTGAGCC-3' (SEQ ID NO:8) and 5'-TTGTCATCGCTTCCAGTCCCCG-3' (SEQ ID NO:9) for responder transgenes. Doxycycline 200 ppm in chow was administered to mice ad libitum to suppress transgene expression. The caspase-2 null (caspase-2Φ/Φ) mice were purchased from the Jackson Laboratory and crossed with the activator (12956-TgtTA) and responder (FVB-Tg4510) mice separately. The offspring 129S6B6F1-TgtTA$^{caspase-2\Phi/+}$ and FVBB6F1-Tg4510$^{caspase-2\Phi/+}$ mice were further crossed to obtain rTg4510$^{caspase-2\Phi/\Phi}$ and rTg4510$^{caspase-2+/+}$ littermates. All experiments with animals were conducted in full accordance with the American Association for the Accreditation of Laboratory Animal Care and Institutional Animal Care and Use Committee at the University of Minnesota.

Behavioral Analysis

Spatial reference memory was measured using the Morris water maze tailored to more rapid learning in the 129FVBF1 background strain (Westerman et al., *J Neurosci*, 2002). Mice were handled 60 seconds per day for 10 days during the 2 weeks before the initiation of testing. Prehandling was designed to condition the mice to manipulations that would be experienced during introduction and removal from the testing pool and included a 20 seconds exposure to water at a depth of 1 cm. Mice then received visible platform training for 3 days (six trials per day) and hidden platform training for 6 days (four trials per day). The spatial cues and hidden platform location were changed at each age tested. Four probe trials of 30 seconds were performed 20 hours after either 8 hours, 12 hours, 16 hours, or 24 hours hidden training trials. The mean platform score and platform crossing index were calculated. All trials were monitored using a computerized tracking system (Noldus EthoVision 3.0; Noldus Information Technology, Wageningen, The Netherlands), and performance measures were extracted using Wintrack (Wolfer et al., *Physiol Behav*, 2001).

Protein Extraction

Mouse brain tissue for biochemical studies was rapidly dissected and quickly frozen for storage at −80° C. To generate forebrain lysates, olfactory bulbs, corticolimbic and subcortical brain stem structures, and the cerebellum were all removed. Frozen hemi-forebrains were thawed and mixed with 1 ml of solution containing 50 mM Tris-HCl (pH 7.4), 150 mM NaCl, 1% Triton X-100, 3% SDS, 1% deoxycholate, phosphate inhibitor cocktail, 0.2 mM 1,10-phenanthroline, 1 mM phenylmethylsulfonyl fluoride, and protease inhibitor cocktail (Sigma-Aldrich, St. Louis, Mo.). Soluble proteins were collected from mechanically homogenized lysates (1 ml syringe, 20 gauge needle [10 repeats]) following centrifugation for 90 minutes at 13,000 rpm. Protein concentrations were measured by using Pierce BCA protein assay kit (Thermo Fisher Scientific, Waltham, Mass.) following manufacturer's instruction.

DNA Constructs

All tau constructs used for transfecting neuronal cultures were tagged with GFP on the N terminus and expressed in the pRK5 vector and driven by a cytomegalovirus (CMV) promoter (Clontech Laboratories, Inc., Mountain View, Calif.) as described in Hoover et al., *Neuron* 2010. The GFP and DsRed constructs (Clontech Laboratories, Inc., Mountain View, Calif.) were also expressed in the pRK5 vector and driven by a CMV promoter. The full-length tau construct encoded human four-repeat tau lacking the N-terminal region (4R0N) and contained exons 1, 4 and 5, 7, and 9-13, intron 13, and exon 14. The GFP-tagged ΔC314 construct was generated from the full-length tau sequence by mutating Leu315 residue to a stop codon with a QuikChange site-directed mutagenesis kit (Stratagene, Agilent Technologies, Inc., Santa Clara, Calif.). To synthesize recombinant tau proteins, full-length tau was subcloned from pRK5 vector into pcDNA3 vector (Invitrogen, Life Technologies Corp., Carlsbad, Calif.) by using BamHI and XhoI restriction sites. A series of truncation mutants including ΔC348, ΔC314, ΔC295 and ΔC283 were generated from the full-length tau construct by mutating Arg349, Leu315, Asn296 and Leu284 to stop codons, respectively. The tau D314E mutant was generated from the full-length tau construct by mutating Asp314 to Glu. Using full-length tau as a template, two tau constructs termed AP or EP were generated by mutating all 14 S/P or T/P amino acid residues (T111, T153, T175, T181, S199, S202, T205, T212, T217, T231, S235, S396, S404, and S422 to Ala (AP) or Glu (EP). All coding sequence authenticity was confirmed by DNA sequencing performed by BioMedical Genomics Center, University of Minnesota.

Caspase Cleavage Assay

Tau proteins (200 ng immunoprecipitates from rTg [tauP301L]4510 or rTg[tauWT]21221 brain lysates, or 1 μl synthetic proteins generated with TNT T7 Quick Coupled Transcription/Translation System [Promega Corp., Madison, Wis.]) were diluted in assay buffer (20 mM HEPES pH 7.2, 10 mM DTT, 1 mM EDTA, 0.1% CHAPS) to a final volume of 50 μl. One unit of recombinant caspase was added to the reactions in the presence or absence of 50 μM z-VAD-fmk (Calbiochem, EMD Biochemicals, San Diego, Calif.). The reactions were incubated at 37° C. for 1.5 hours and stopped by adding Laemmli sample buffer (62.5 mM Tris-HCl [pH 6.8], 25% glycerol, 2% SDS, and 0.01% bromophenol blue). The reactions were then subjected to western blotting and revealed with Tau-13 antibody (Covance Inc., Princeton, N.J.).

Western Blotting and Densitometric Analysis

Five micrograms of rTg(tauP301L)4510 mouse brain lysates were electrophoresed on 10% Tris-HCl gels (Bio-Rad Laboratories, Inc., Hercules, Calif.), then transferred onto 0.45 μm polyvinylidene difluoride membranes (Millipore Corp., Billerica, Mass.). Membranes were blocked in 5% BSA and probed with primary antibody Tau-13 (Covance Inc., Princeton, N.J.), and visualized using enhanced chemiluminescence reagents (Thermo Fisher Scientific, Waltham, Mass.) followed by exposure onto hyperfilm (Kodak). βIII-Tubulin was also probed as loading controls. Densitometric analysis of protein signal was performed using the ImageJ software (NIH).

Tau H1485 Antibody Production

Rabbit polyclonal H1485 antibody was generated against a cleavage peptide corresponding to the C terminus of tau truncated at Asp314 by using custom antibody service (New England Peptide LLC, Gardner, Mass.). Specifically, the peptide Ac-CIVYKPVD-OH (SEQ ID NO:10), which corresponds to tau residues 308-314 with a Cys added to the N terminus, was synthesized. This peptide was coupled through the Cys to keyhole limpet hemocyanin. Rabbits were immunized with the cleavage peptide three times over a period of four weeks. Seven and twelve days after the final immunization, the rabbits were bled and their sera were collected, respectively. The sera were combined and incubated with an affinity column using a spanning peptide (Ac-CIVYKPVDL-SKVT-amide, SEQ ID NO:11) which corresponds to tau residues 308-319 with a Cys residue added to the N-terminus.

The flow-through from this column was then incubated with an affinity column using the cleavage peptide. The cleavage-site specific antibody H1485 was then eluted off the column and stored at −20° C.

Immunoprecipitation Assay

Fifty micrograms of rTg[tauP301L]4510 brain lysates were diluted in 1 ml lysis buffer (50 mM Tris-HCl pH 7.4, 150 mM NaCl, 0.2 mM 1,10-phenanthroline, 1 mM phenylmethylsulfonyl fluoride, and protease inhibitor cocktail) and incubated at 4° C. overnight under agitation in the presence of 5 μg Tau-13 antibody. Twenty microliters of Protein G Sepharose beads (GE Healthcare, UK) were added to the samples. The samples were further incubated for 2 hours and then centrifuged. The supernatant was discarded and the beads were washed in lysis buffer three times. Finally, the proteins were eluted off by adding 40 μl Laemmli sample buffer to the beads. The immunoprecipitated proteins were analyzed with western blotting.

Primary Neuronal Culture and Transfection

Based on methods described in Hoover et al., *Neuron* 2010, dissociated rat hippocampal primary neuron cultures were prepared. Briefly, a 25 mm glass coverslip (thickness, 0.08 mm) was glued over a 22 mm hole in the bottom of a 35 mm tissue culture dish using silicone sealant. Dissociated neuronal cultures from rat hippocampi at P1 were prepared. Neurons were plated onto prepared 35 mm tissue culture dishes at a density of $1 \times 10^6$ cells per dish. The age of cultured neurons was counted from the day of plating (1 DIV). Neurons at 7 DIV were transfected using a standard calcium phosphate precipitation method and allowed to grow to maturity (>3 weeks) to be imaged. Neurons were transfected with equivalent concentrations of plasmids encoding full-length tau or tau ΔC314 mutant. The plasmid encoding DsRed was cotransfected with tau constructs to visualize dendritic spines.

Image Analysis of Living Neurons

Coverslips of neurons cotransfected with various GFP-tagged tau constructs and DsRed were photographed on an inverted Nikon epifluorescent microscope with a 60× oil lens and a computerized focus motor at 21-35 DIV. All digital images were photographed and processed with MetaMorph Imaging System (Universal Imaging Corporation, West Chester, Pa.). All images were taken as stacks (15 planes at 0.5 micron increments) and processed by deconvolution analyses using the MetaMorph software with the nearest planes and averaged into one single image. A dendritic protrusion with an expanded head that was 50% wider than its neck was defined as a spine.

Electrophysiological Analysis

Miniature excitatory postsynaptic potentials (mEPSCs) were recorded at −55 mV in artificial cerebrospinal fluid (aCSF) containing 100 μM AP7 (NMDAR antagonist, Tocris Bioscience, UK), 1 μM TTX (sodium channel blocker, Tocris Bioscience, UK) and 50 μM bicuculline (GABA receptor antagonist, Sigma-Aldrich, St. Louis, Mo.). Electrophysiology experiments were conducted using AXON DIGIDATA 1440A data acquisition system (Molecular Devices, LLC, Sunnyvale, Calif.), AXOPATCH 200B amplifier (Molecular Devices, LLC, Sunnyvale, Calif.), pCLAMP10 software (Molecular Devices, LLC, Sunnyvale, Calif.). Data was analyzed using AxoGraph X software (Berkeley, Calif.).

Screening Assay

Unless otherwise stated, chemicals were purchased from Sigma-Aldrich (St. Louis, Mo.). Caspase-2 was made in-house; reference Caspase-2 inhibitor Z-VAD-FMK was purchased from BD Pharmingen (San Diego, Calif.). The fluorescently labeled substrate for Caspase-2, FITC-AHX-GSVQIVYKPVDLSKVTS-COOH, was custom synthesized by Celtek Peptides (Franklin, Tenn.). Assay buffer contained 20 mM HEPES, pH 7.2, 1 mM EDTA, 0.1% CHAPS, and 10 mM DTT.

In black, Greiner 384-well plates, 80 μL of assay buffer was added to each well; wells that were not screened for compounds contained only this buffer. For reagent wells, 4 μL of compound (or 4 μL of buffer as a control) and 15 μL of Caspase-2 (30 U/μL) were added to the buffer. After a 10-minute incubation at room temperature, 1 μL of 0.5 mM substrate in 50% DMSO was added to each reagent well (for a final substrate concentration of 5 μM/well); plates were then incubated at 37° C. After 1.5 hours of incubation, 10 μL of stop solution (8.0 pH buffer containing 0.1% coating-3 reagent (Caliper Life Sciences Inc., Hopkinton, Mass.)) was added to each well.

Plates were screened in a LabChip 3000 (Caliper Life Sciences Inc., Hopkinton, Mass.) with temperature and relative humidity set to 20° C. and 50%. A 12-sipper chip sampled contents from each well and measured the fluorescent intensity of the substrate and product peaks. For optimal electrophoretic separation of substrate and product peaks, a separation buffer consisting of ProfilerPro separation buffer and 0.1% coating-3 reagent (Caliper Life Sciences Inc., Hopkinton, Mass.) was run through the LC3000, and a pressure of −1.0 psi and a voltage of −1700ΔV (−1200V/−2900V) were applied during the screening process. Data were analyzed using Caliper's HTS Well Analyzer software.

Example 2

Protein Extraction

Mouse brain tissue for biochemical studies was rapidly dissected and quickly frozen for storage at −80° C. To generate forebrain lysates, olfactory bulbs, corticolimbic and sub-cortical brain stem structures, and the cerebellum were all removed. Frozen hemi-forebrains were thawed and mixed with 1 ml of solution containing 50 mM Tris-HCl (pH 7.4), 150 mM NaCl, 1% Triton X-100, 3% SDS, 1% deoxycholate, phosphate inhibitor cocktail, 0.2 mM 1,10-phenanthroline, 1 mM phenylmethylsulfonyl fluoride, and protease inhibitor cocktail (Sigma). Soluble proteins were collected from mechanically homogenized lysates (1 ml syringe, 20 gauge needle [10 repeats]) following centrifugation for 90 min at 13,000 rpm. Protein concentrations were measured by using Pierce BCA protein assay kit (Thermo Fisher Scientific, Waltham, Mass.) following manufacturer's instruction.

A cohort of 85 human tissue samples was obtained from the Memory and Aging Project, Rush University. These samples represent elderly people with no cognitive impairment (NCI), mild cognitive impairment (MCI) and Alzheimer's disease (AD). The prefrontal cortex of these samples was homogenized in solution containing 50 mM Tris-HCl (pH 7.6), 0.01% NP-40, 150 mM NaCl, 2 mM EDTA, 0.1% SDS, 1 mM phenylmethylsulfonyl fluoride, and protease inhibitor cocktail (Sigma-Aldrich, St. Louis, Mo.) and centrifuged for 90 min at 3,000 rpm. The pellet was further extracted in solution containing 50 mM Tris-HCl pH 7.6, 150 mM NaCl, 0.1% Triton X-100 and centrifuged for 90 min at 13,000 rpm. Protein concentrations of the supernatant were measured by using Pierce BCA protein assay kit (Thermo Fisher Scientific, Waltham, Mass.) following manufacturer's instruction. Results are shown in FIG. 14.

Immunoprecipitation Assay

Fifty micrograms of rTg[tauP301L]4510 brain lysates were diluted in 1 ml lysis buffer (50 mM Tris-HCl pH 7.4, 150 mM NaCl, 0.2 mM 1,10-phenanthroline, 1 mM phenylmethylsulfonyl fluoride, and protease inhibitor cocktail) and incubated at 4° C. overnight under agitation in the presence of 5 μg Tau-13 antibody (Covance Inc., Princeton, N.J.). Three hundred micrograms of human tissue lysates were diluted in 1 ml lysis buffer and incubated at 4° C. overnight under agitation in the presence of 30 μg Tau-13 antibody (Covance Inc., Princeton, N.J.). Twenty microliters of Protein G Sepharose beads (GE Healthcare, UK) were added to the samples. The samples were further incubated for 2 h and then centrifuged. The supernatant was discarded and the beads were washed in lysis buffer three times. Finally, the proteins were eluted off by adding 40 μl Laemmli sample buffer to the beads. The immunoprecipitated proteins were analyzed with western blotting by using H1485 antibody.

Western Blotting and Densitometric Analysis

Five micrograms of rTg(tauP301L)4510 mouse brain lysates were electrophoresed on 10% Tris-HCl gels (Bio-Rad Laboratories, Inc., Hercules, Calif.), then transferred onto 0.45 μm polyvinylidene difluoride membranes (Millipore Corp., Billerica, Mass.). Membranes were blocked in 5% BSA and probed with primary antibody Tau-13 (Covance Inc., Princeton, N.J.), and visualized using enhanced chemiluminescence reagents (Thermo Fisher Scientific, Waltham, Mass.) followed by exposure onto hyperfilm (Kodak). Human tissue lysates were probed with H1485 antibody, 8E6/C11 antibody (Millipore), 1E1/A6 antibody (Millipore), and Tau-13 antibody (Covance Inc., Princeton, N.J.). Densitometric analysis of protein signal was performed using the ImageJ software (NIH). Results are shown in FIG. 13.

Primary Neuronal Culture and Transfection

Based on methods described in Hoover et al., *Neuron* 2010, dissociated rat hippocampal primary neuron cultures were prepared. Briefly, a 25 mm glass coverslip (thickness, 0.08 mm) was glued over a 22 mm hole in the bottom of a 35 mm tissue culture dish using silicone sealant. Dissociated neuronal cultures from rat hippocampi at P1 were prepared. Neurons were plated onto prepared 35 mm tissue culture dishes at a density of $1 \times 10^6$ cells per dish. The age of cultured neurons was counted from the day of plating (1 DIV). Neurons at 7 DIV were transfected using a standard calcium phosphate precipitation method and allowed to grow to maturity (>3 weeks) to be imaged. Neurons were transfected with equivalent concentrations of constructs encoding various tau proteins. The plasmid encoding DsRed was cotransfected with tau constructs to visualize dendritic spines. Recombinant tau protein or TCP35 protein (10 μM) was directly added to culture medium 1 hour before imaging to stimulate neuronal cultures. Caspase-2-selective inhibitor Ac-VDVAD-CHO (SEQ ID NO:36; Sigma-Aldrich, St. Louis, Mo.) or caspase-3-selective inhibitor Ac-DEVD-CHO (SEQ ID NO:37; Promega Corp., Madison, Wis.) was directly added to culture medium 2 days before imaging to block caspase-2 or caspase-3 activity.

Image Analysis of Living Neurons

Coverslips of neurons cotransfected with various GFP-tagged tau constructs and DsRed were photographed on an inverted Nikon epifluorescent microscope with a 60× oil lens and a computerized focus motor at 21-35 DIV. All digital images were photographed and processed with MetaMorph Imaging System (Universal Imaging Corporation, West Chester, Pa.). All images were taken as stacks (15 planes at 0.5 micron increments) and processed by deconvolution analyses using the MetaMorph software with the nearest planes and averaged into one single image. A dendritic protrusion with an expanded head that was 50% wider than its neck was defined as a spine. Results are shown in FIG. 15 and FIG. 16.

Expression and Purification of Recombinant Protein in *E. coli*

Recombinant tau and TCP35 proteins were expressed by using pET system (Novagen, EMD Millipore, Billerica, Mass.) following manufacturer's instruction. Briefly, the coding sequences of tau and TCP35 were cloned into pET28a vector, respectively. The expression constructs were transformed in BL21(DE3) *E. coli*. The expression of recombinant proteins was induced by 1 mM isopropyl β-D-1-thiogalactopyranoside at 37° C. for 3 hours. The recombinant proteins were purified from *E. coli* cell lysates by using immobilized metal affinity chromatography (Thermo Fisher Scientific, Waltham, Mass.) following manufacturer's instruction.

Example 3

The pentapeptides shown in Table 1 were synthesized using a solid support and accompanied by microwave irradiation to heat the reaction mixture during coupling and N(α)-deprotection.

Solid Phase Peptide aldehyde Synthesis

The pentapeptides were synthesized using 0.05 mmol (250 mg) scale of H-asp(OtBu)—H preloaded aldehyde resin (AnaSpec. Inc., Fremont, Calif.) following the manufacturer's instructions. Briefly, the H-asp(OtBu)—H preloaded resin allows the synthesis of peptides containing C-terminal aspartinal. The peptide aldehyde synthesis is carried out using standard instrument protocols. Cleavage from the resin and side-chain deprotection is performed in two stages. It enables side-products from side-chain deprotection to be removed by washing before the product is released into aqueous solution.

The resin was added to a 20 mL fritted glass tube and was swollen for 2-16 hours in DCM (dichloromethane; Sigma-Aldrich, St. Louis, Mo.). The DCM was then removed from resin and it was washed 3 times with DMF (N,N'-dimethylformamide from Sigma-Aldrich, St. Louis, Mo.) using one minute mix times.

Amino acids were coupled using FmocAA (9-N-fluorenylmethyloxycarbonyl amino acids from Sigma-Aldrich, St. Louis Mo.) (3 equivalents), HOBt (hydroxybenzotriazole from Sigma-Aldrich, St. Louis, Mo.) 3.1 equivalents, 0.155 mmol, 21 mg), DIC (diisopropopylcarbodiimide from Sigma-Aldrich, St. Louis, Mo.) (3.2 equivalents, 0.16 mmol, 25 μL) were dissolved in the same vial in anhydrous DMF (2-3 mL) and then added to the resin. The resin pre-stirred for 30 seconds, then heated to 65° C. for 15 minutes in a 55 W microwave oven. The resin was filtered and washed three times with 3 mL aliquots of DMF using 1 minute mix time for each. The ninhydrin test (AnaSpec. Inc., Fremont, Calif.) was performed to evaluate the completion of the coupling reaction according to the manufacturer's instructions.

To deprotect the N-terminal α-amine group, a 20% v/v solution of piperidine in DMF (0.6 mL/3 mL) was added to the resin. The resin pre-stirred for 30 seconds, then heated to 65° C. for 10 minutes in a 55 W microwave oven. The resin was filtered and washed three times with 3 mL aliquots of DMF (1 minute each). The ninhydrin test was performed according to the manufacturer's instructions, the resin was rinsed three times with DCM (3 mL) and then dried under vacuum for 10 minutes.

If a terminal N—Ac-aa was not commercially available, following the last deprotection, a solution of acetic anhydride/N,N'-diisopropylethylamine/N,N'-dimethylformamide (Ac$_2$O/DIPEA/DMF, 3/1/96 (5 mL), all components from Sigma-Aldrich, St. Louis, Mo.) was added to the resin and the mixture was stirred for 15 minutes at room temperature. The resin was then rinsed three times with DCM and dried under vacuum.

Deprotection of lateral chains was performed using 3 mL of TFA was added in the fritted glass tube and the mixture was stirred bubbled with nitrogen for 30 minutes at room temperature. The resin was filtered and washed with DCM (5 mL).

Finally a solution of $CH_3CN$/water (60/40; v/v) with 0.1% TFA was used for the cleavage from the resin. 5 mL of the solution were added and the mixture was stirred twice for 30 minutes at room temperature followed by filtration and washing with two further aliquots of mixture $CH_3CN$/water (60/40) with 0.1% TFA. The filtrate was lyophilized to give the crude product which was purified using a preparative HPLC (GEMINI 5 µm C18 110 A, 150×10 mm from Phenomenex Inc., Torrence, Calif.; gradient 5% to 100% of acetonitrile in water+0.1% formic acid over 10 minutes) to afford the final pentapeptide aldehyde product.

Example 4

Tau Aptamer Production

Sequences for aptamer selection are prepared using standard peptide chemistry or resourced. The sequence for selection can be as short as a 5-mer (e.g., SEQ ID NO:1) or as long as the 314-amino acid cleavage product (e.g., SEQ ID NO: 13), and are chosen based on empirical results. Selection of aptamers is performed using systematic evolution of ligands by an exponential enrichment (SELEX) methods as previously described (Takemura, et al. *Exp. Biol. Med.* (*Maywood*) 2006, 231:204-214; Wongphatcharachai, et al. *J. Clin. Microbiol.* 2013, 51:46-54.). Counter-selection is performed using the full-length tau protein.

As used herein, the term "and/or" means one or all of the listed elements or a combination of any two or more of the listed elements; the terms "comprises" and variations thereof do not have a limiting meaning where these terms appear in the description and claims; unless otherwise specified, "a," "an," "the," and "at least one" are used interchangeably and mean one or more than one; the recitations of numerical ranges by endpoints include all numbers subsumed within that range (e.g., 1 to 5 includes 1, 1.5, 2, 2.75, 3, 3.80, 4, 5, etc.); and reference to relative terms such as, for example, increase, decrease, or delay refers to comparison with an appropriate control including, where appropriate, an individual or population of individuals not receiving the indicated treatment.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

| Sequence Listing Free Text | |
|---|---|
| YKPVD | SEQ ID NO: 1 |
| AHX-GSVQIVYKPDLSKVTS | SEQ ID NO: 2 |
| AHX-GSVQIVYKPVD | SEQ ID NO: 3 |
| AHX-GSVQIVYK(acetyl)PVDLSKVTS | SEQ ID NO: 4 |
| AHX-GSVQIVYK(acetyl)PVD | SEQ ID NO: 5 |
| GATTAACAGC GCATTAGAGC TG | SEQ ID NO: 6 |

What is claimed is:

1. An antibody preparation comprising a monoclonal antibody that specifically binds to SEQ ID NO:11 and requires no amino acid residues outside of SEQ ID NO:11 to specifically bind to SEQ ID NO:11.

2. A method comprising:
contacting a biological sample comprising cerebral spinal fluid from a subject with an antibody preparation of claim 1; and
detecting a ligand in the sample that specifically binds the antibody preparation.

3. The method of claim 2 wherein the subject exhibits at least one symptom or clinical sign of a tauopathic condition.

4. The method of claim 3 wherein the tauopathic condition is Alzheimer's disease.

5. The method of claim 2 wherein the subject exhibits no symptom or clinical sign of a tauopathic condition.

6. The method of claim 2 wherein the tauopathic condition is Alzheimer's disease.

\* \* \* \* \*